United States Patent
Shindo et al.

(10) Patent No.: US 10,206,635 B2
(45) Date of Patent: Feb. 19, 2019

(54) X-RAY COMPUTED TOMOGRAPHY APPARATUS AND GANTRY

(71) Applicant: Toshiba Medical Systems Corporation, Otawara-shi (JP)

(72) Inventors: Yasutaka Shindo, Nasushiobara (JP); Hiroki Osaki, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 155 days.

(21) Appl. No.: 15/297,621

(22) Filed: Oct. 19, 2016

(65) Prior Publication Data

US 2017/0105691 A1 Apr. 20, 2017

(30) Foreign Application Priority Data

Oct. 20, 2015 (JP) .................................. 2015-206417
Oct. 17, 2016 (JP) .................................. 2016-203791

(51) Int. Cl.
*A61B 6/00* (2006.01)
*A61B 6/03* (2006.01)

(52) U.S. Cl.
CPC ............ *A61B 6/035* (2013.01); *A61B 6/4447* (2013.01); *A61B 6/5205* (2013.01); *A61B 6/4488* (2013.01)

(58) Field of Classification Search
None
See application file for complete search history.

(56) References Cited

U.S. PATENT DOCUMENTS

| | | | |
|---|---|---|---|
| 7,188,998 B2 * | 3/2007 | Gregerson | A61B 6/02 378/197 |
| 2011/0249806 A1 * | 10/2011 | Wendlandt | A61B 6/4405 378/198 |

FOREIGN PATENT DOCUMENTS

| | | |
|---|---|---|
| EP | 0 495 137 A1 | 7/1992 |
| JP | 2-123211 U | 10/1990 |
| JP | 4-317635 | 9/1992 |
| JP | 2008-278902 | 11/2008 |
| JP | 2012-45294 | 3/2012 |
| JP | 2013-9819 | 1/2013 |

\* cited by examiner

*Primary Examiner* — Hoon K Song
(74) *Attorney, Agent, or Firm* — Oblon, McClelland, Maier & Neustadt, L.L.P.

(57) ABSTRACT

According to one embodiment, an X-ray computed tomography apparatus includes a gantry for imaging a subject by X-ray CT and a console communicably connected to the gantry. The gantry includes a gantry body and a column unit. The gantry body has a bore into which the subject is inserted when the subject is imaged by X-ray CT. The column unit includes a first column which supports the gantry body slidably in a direction perpendicular to a floor surface and a second column which supports the first column slidably in a vertical direction.

13 Claims, 16 Drawing Sheets

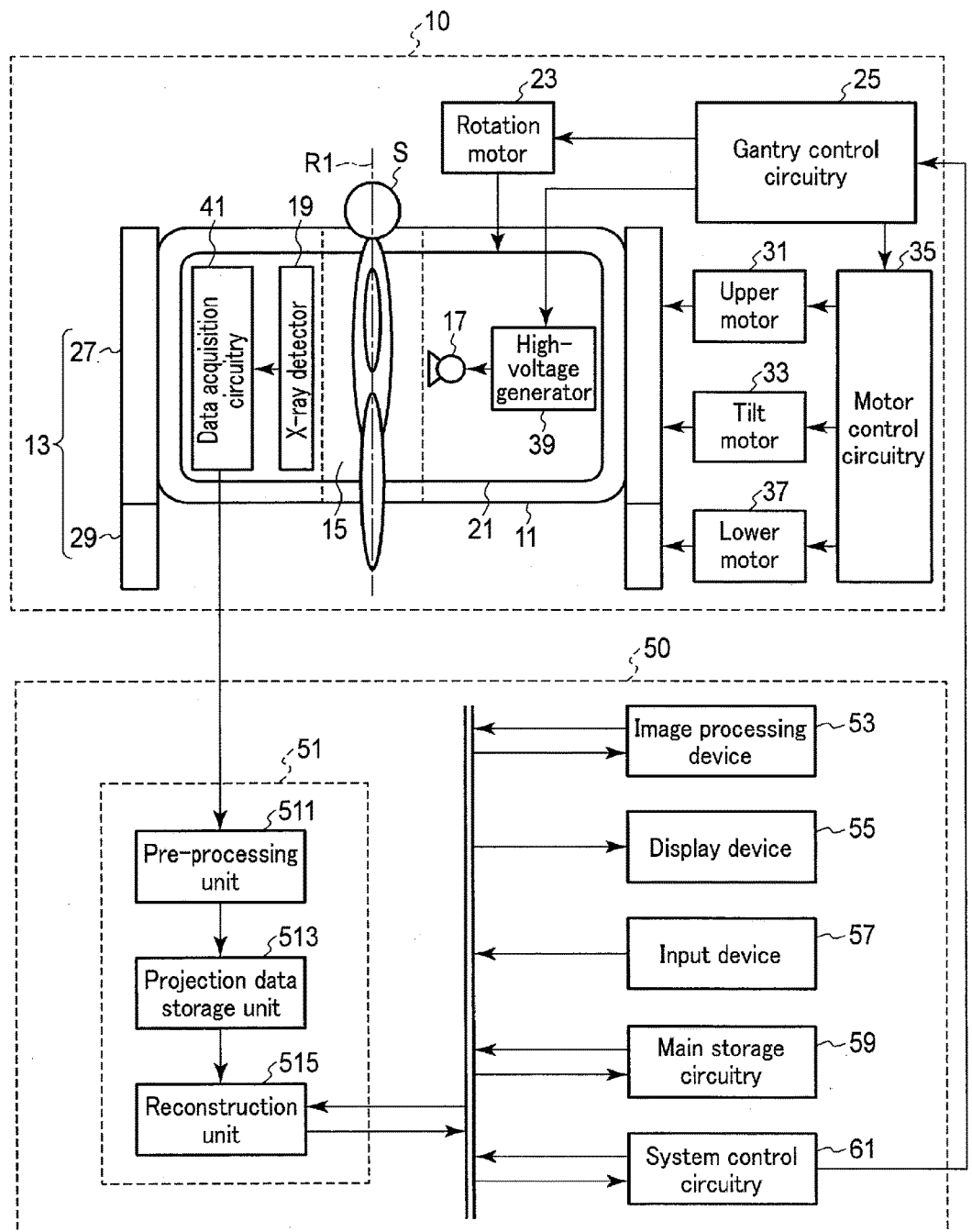
F I G. 1

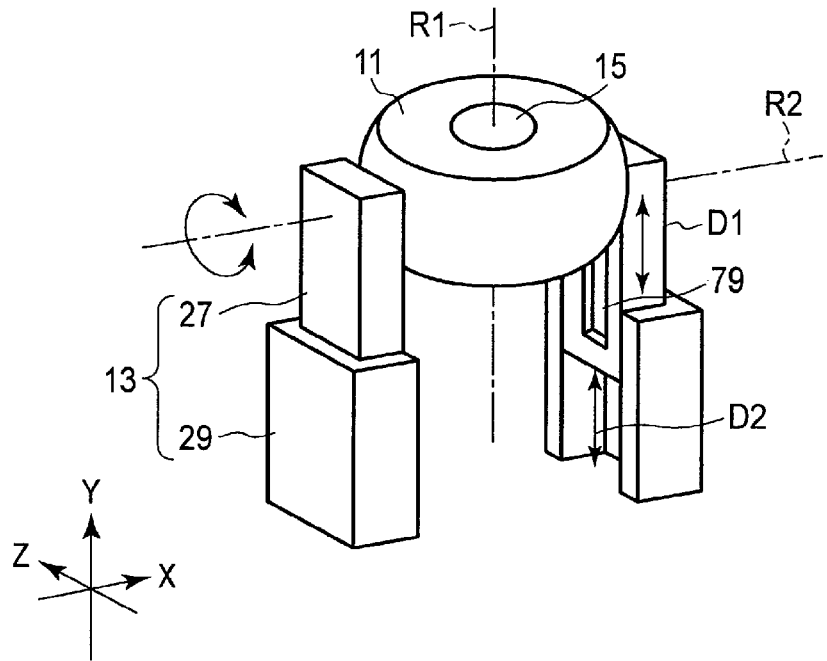
F I G. 2
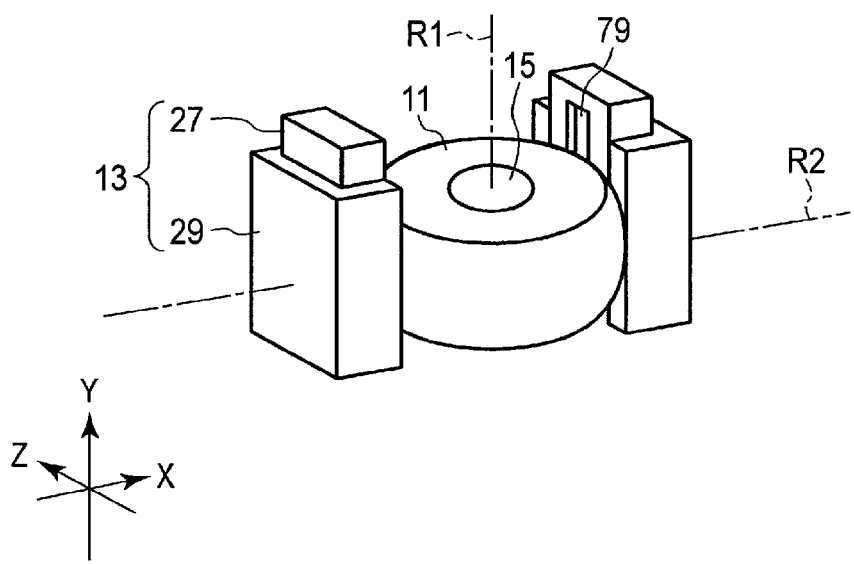
F I G. 3

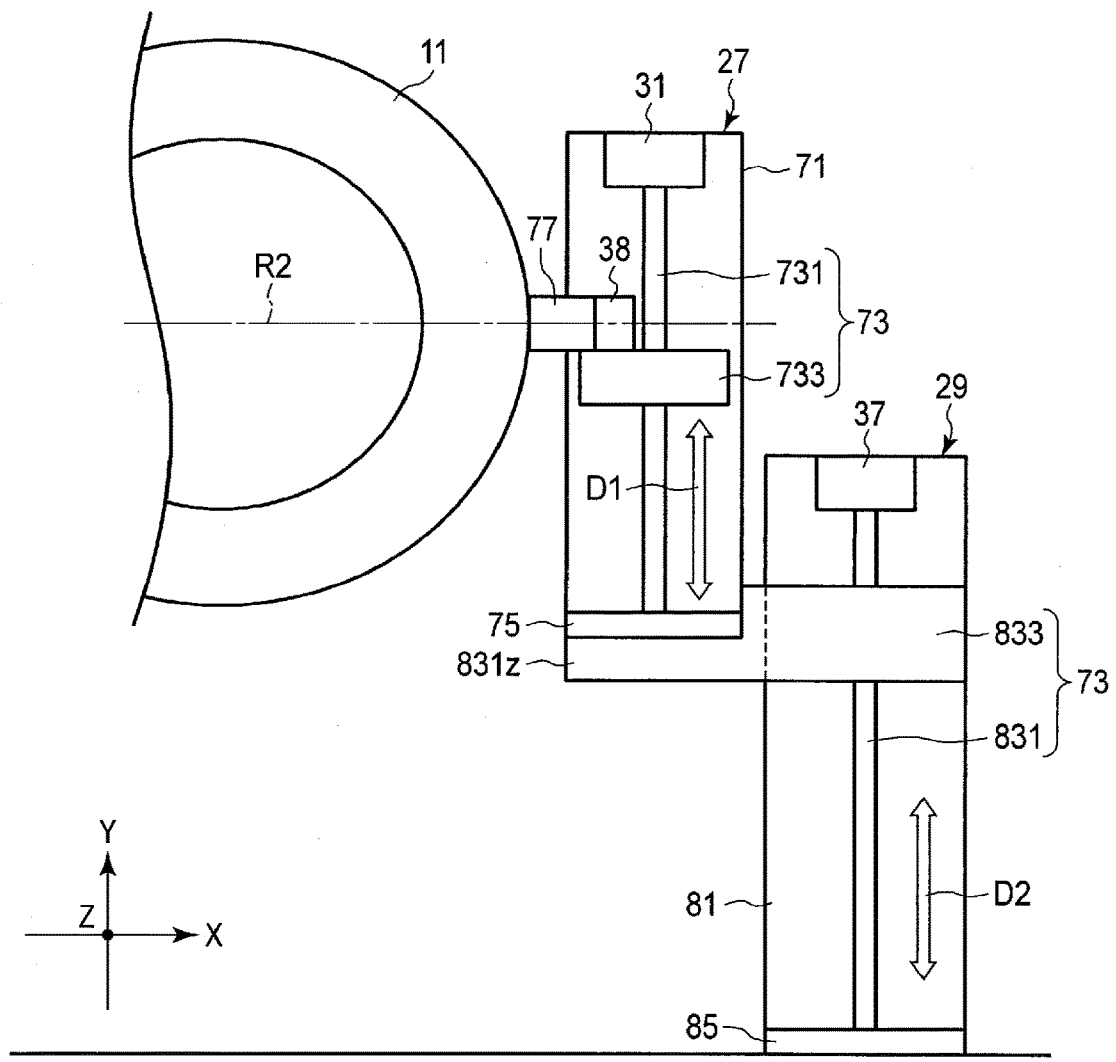
F I G. 5

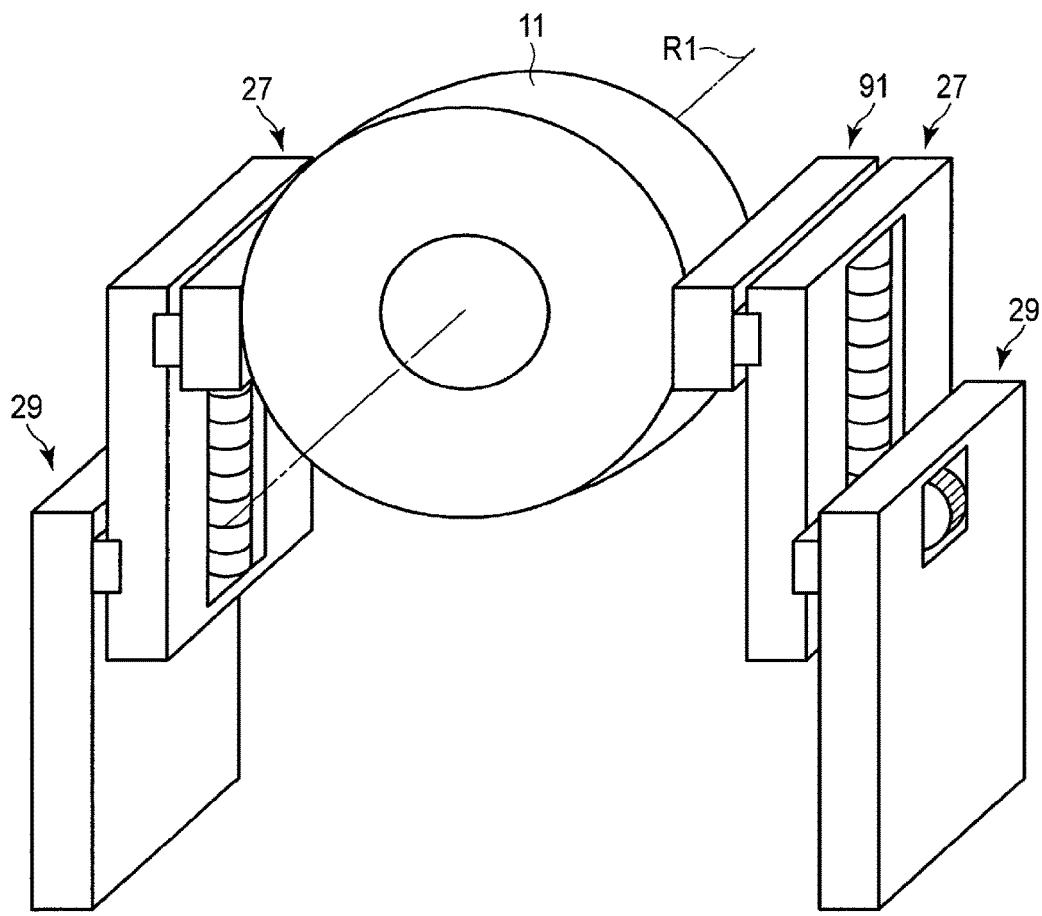
F I G. 10

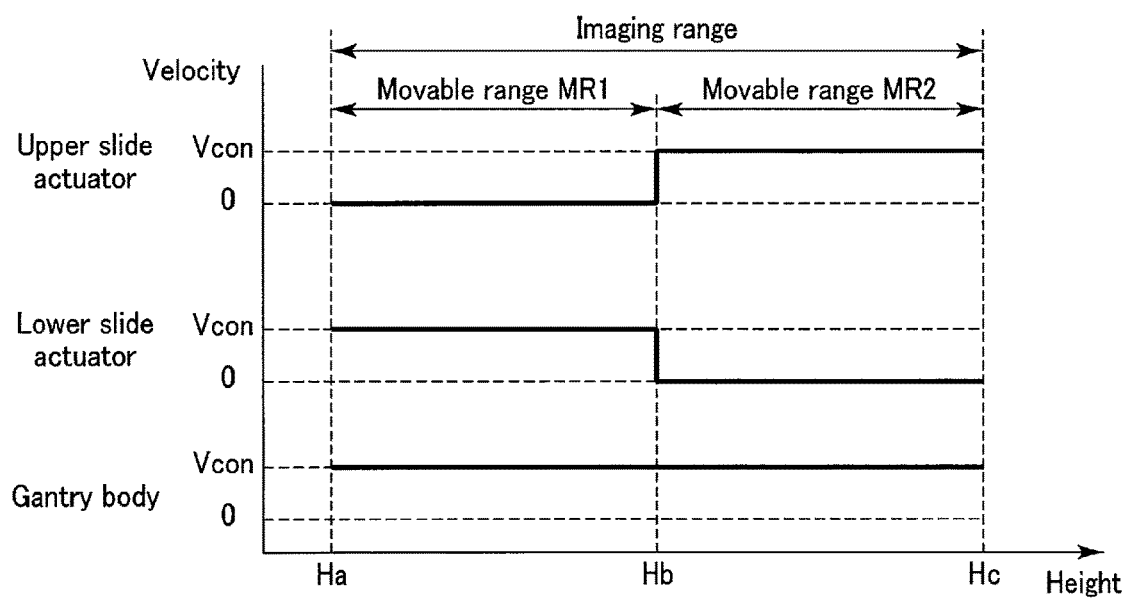
F I G. 13

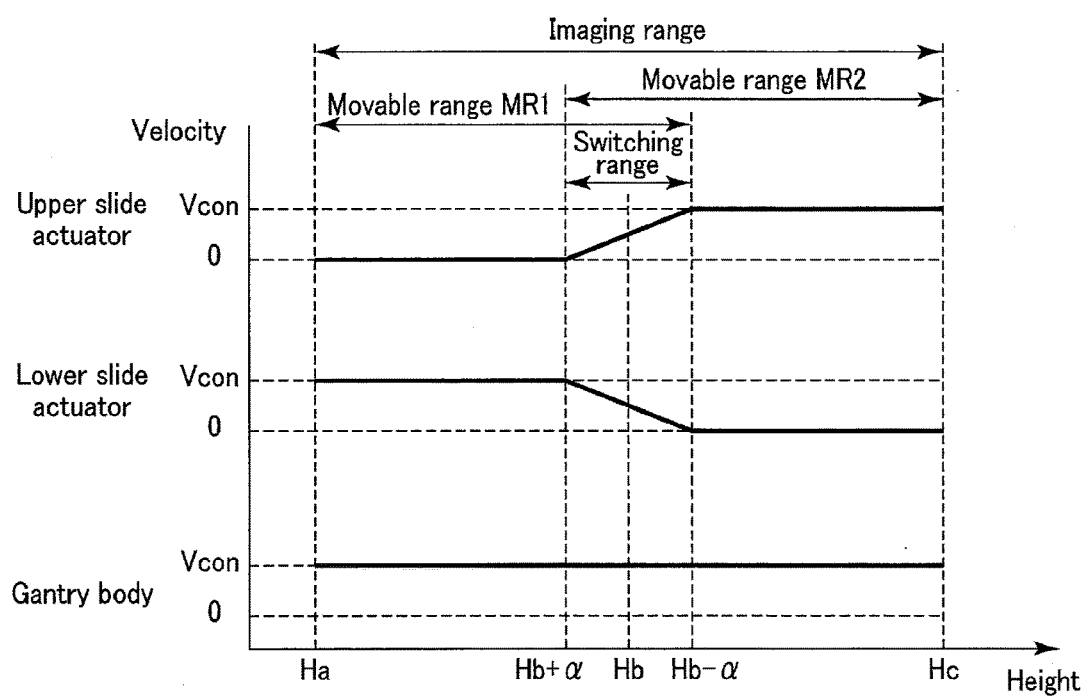
F I G. 15

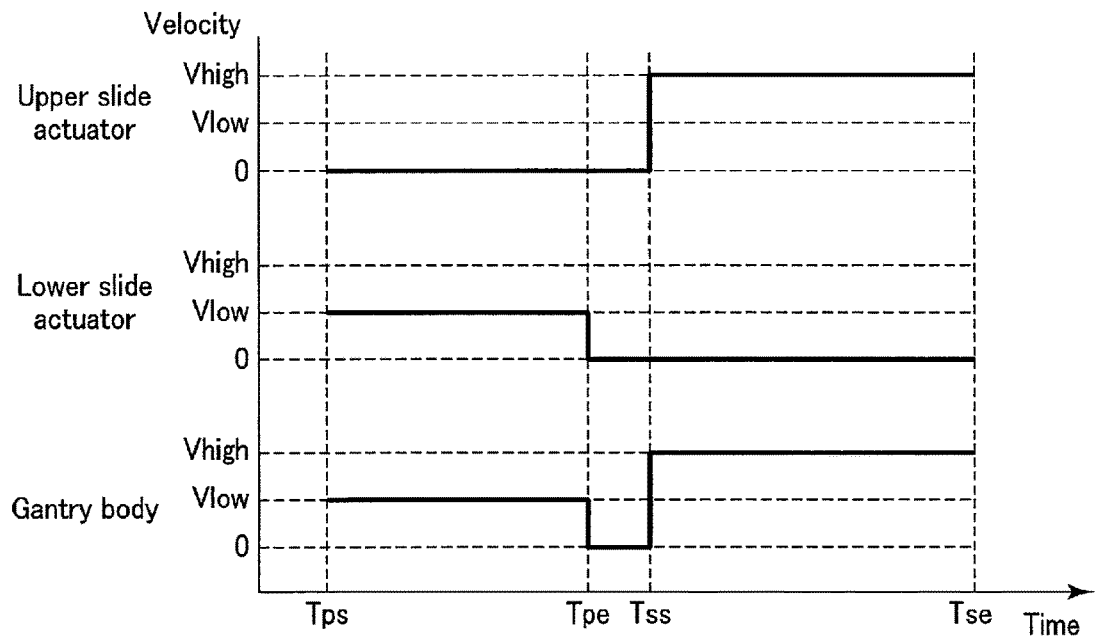
F I G. 17A
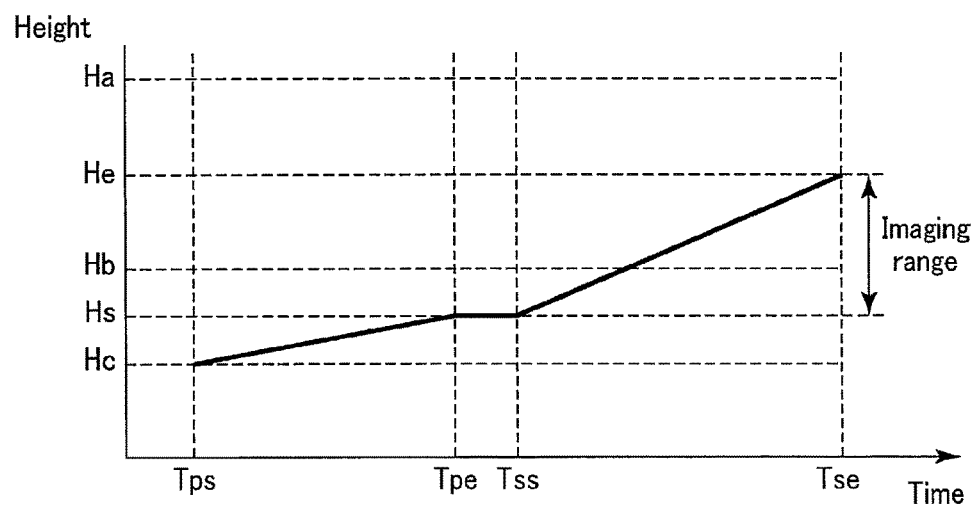
F I G. 17B

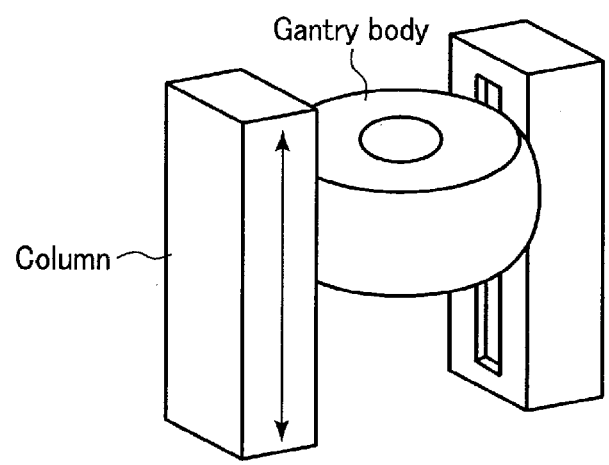
F I G. 18
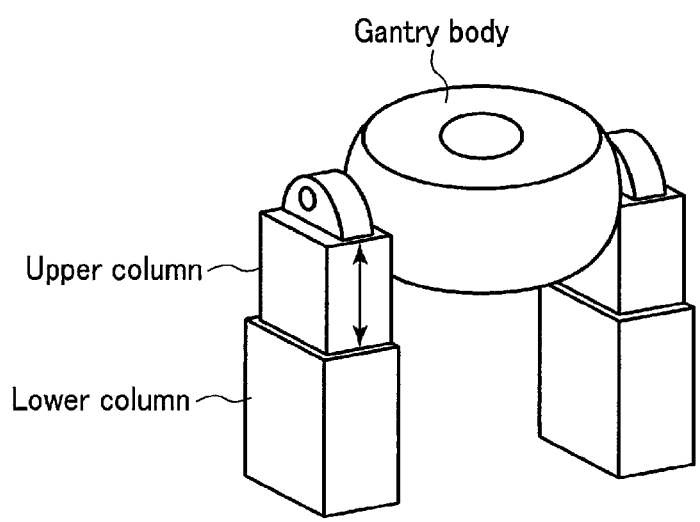
F I G. 19

US 10,206,635 B2

X-RAY COMPUTED TOMOGRAPHY APPARATUS AND GANTRY

CROSS-REFERENCE TO RELATED APPLICATIONS

This application is based upon and claims the benefit of priority from the prior Japanese Patent Application No. 2015-206417, filed Oct. 20, 2015 and prior Japanese Patent Application No. 2016-203791, filed Oct. 17, 2016, the entire contents of all of which are incorporated herein by reference.

FIELD

Embodiments described herein relate generally to an X-ray computed tomography apparatus and a gantry.

BACKGROUND

X-ray computed tomography is usually performed for a patient who is in the lying position on a bed. However, when X-ray computed tomography is used to diagnose deglutition disorder and the like, it is desirable that a patient be in the standing position. X-ray computed tomography for patients in the standing position has not yet been put to practical use.

BRIEF DESCRIPTION OF THE DRAWINGS

FIG. 1 is a block diagram showing a structure of an X-ray computed tomography apparatus according to an embodiment.

FIG. 2 is an external view of a gantry whose gantry body is located at the maximum height such that its central axis R1 extends in the vertical Y direction.

FIG. 3 is an external view of the gantry whose gantry body is located at the minimum height such that its central axis R1 extends in the vertical Y direction.

FIG. 5 is a cross-sectional view of the gantry shown in FIG. 1.

FIG. 10 is a perspective view of the gantry shown in FIG. 6, the gantry body of which is located at the maximum height.

FIG. 13 is a chart showing an example of an operation sequence in a whole-body imaging mode for individual drive, which is performed by the motor control circuitry shown in FIG. 1.

FIG. 15 is a chart showing another example of the operation sequence in the whole-body imaging mode for individual drive, which is performed by the motor control circuitry shown in FIG. 1.

FIGS. 17A and 17B is a chart showing an operation sequence for partial imaging, which is performed by the motor control circuitry shown in FIG. 1.

FIG. 18 is an external view of a column fixed type gantry.

FIG. 19 is an external view of a column stored type gantry.

DETAILED DESCRIPTION

Figure 4:
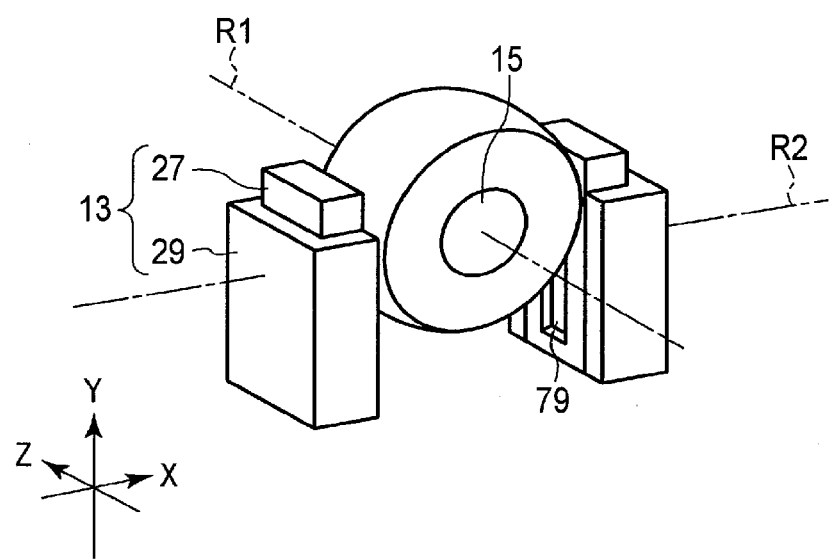
FIG. 4 is an external view of the gantry whose gantry body is located such that its central axis R1 extends in the horizontal Z direction.

In general, according one embodiment, an X-ray computed tomography (CT) apparatus includes a gantry designed to perform X-ray CT for a subject and a console communicably connected to the gantry. The gantry includes a gantry body and a column unit. The gantry body has a bore into which the subject is inserted for the CT. The column unit includes a first support for supporting the gantry body slidably in a direction perpendicular to the floor surface and a second support for supporting the first support slidably in the vertical direction.

The X-ray CT apparatus and gantry according to the present embodiment will be described below with reference to the drawings.

FIG. 1 is a block diagram of the X-ray computed tomography apparatus according to the present embodiment. As shown in FIG. 1, the X-ray computed tomography apparatus includes a gantry 10 and a console 50. For example, the gantry 10 is placed in a CT examination room and the console 50 is placed in a control room adjacent to the CT examination room. The gantry 10 and the console 50 are communicably connected to each other by wire or wirelessly. The gantry 10 is a scanner that is configured to perform X-ray computed tomography (referred to as X-ray CT hereinafter) for subjects in the standing position. The console 50 is a computer for controlling the gantry 10.

The gantry 10 includes a gantry body 11 and a column unit 13. FIG. 2 is an external view of the gantry 10 whose gantry body 11 is located at the highest position. FIG. 3 is an external view of the gantry 10 whose gantry body 11 is located at the lowest position. Hereinafter, the vertical direction is defined as a Y direction, a direction parallel to a horizontal axis R2 which is horizontally orthogonal to a central axis R1 of a bore 15 of the gantry body 11 is defined as an X direction, and a direction orthogonal to the X direction and Y directions is defined as a Z direction.

As shown in FIGS. 2 and 3, the gantry body 11 is a substantially cylindrical-shaped structure in which the bore 15 is formed to make a field of view. As shown in FIG. 1, the gantry body 11 includes an X-ray tube 17 and an X-ray detector 19 which are opposed to each other with the bore 15 therebetween.

More specifically, the gantry body 11 further includes a main frame (not shown) formed of metal such as aluminum and a rotation frame 21 that is supported rotatably around the central axis R1 through, e.g. bearings by the main frame. A slip ring (not shown) is provided at a contact portion of the main frame with the rotation frame 21. A conductive brush (not shown) is attached to the contact portion of the main frame to be brought into slidable contact with an annular electrode. The rotation frame 21 is a metal frame formed annularly by metal such as aluminum. For example, the X-ray tube 17 and X-ray detector 19 are attached to the rotation frame 21. The X-ray tube 17 and X-ray detector 19 can be fitted into a concave portion formed in the rotation frame 21 or fastened together by a fastening device such as a screw.

Upon receiving power from a rotation motor 23, the rotation frame 21 rotates around the central axis R1 with constant angular velocity. The rotation motor 23 generates power to rotate the rotation frame 21 according to the control from gantry control circuitry 25. The power is generated by driving the rotation motor 23 at a rotational speed corresponding to, e.g. the duty ratio of a drive signal from the gantry control circuitry 25. The rotation motor 23 is achieved by a motor such as a direct drive motor and a servo motor. The rotation motor 23 is contained in, for example, the gantry body 11.

As shown in FIGS. 2 and 3, the column unit 13 is a base for supporting the gantry body 11 at an interval from the floor surface. Specifically, the column unit 13 has a two-stage structure of an upper column 27 and a lower column 29 in order to avoid increasing in size and allow X-ray CT for the whole body of subject S.

The upper column 27 is a structure for supporting the gantry body 11 slidably in a longitudinal direction D1 of the upper column 27. The upper column 27 is shaped like a pillar such as a cylinder and a prism. The upper column 27 is formed of an arbitrary material such as plastic and metal. The upper column 27 is attached to one side of the gantry body 11. The upper column 27 has a structure to allow the gantry body 11 to be supported such that the central axis R1 of the bore 15 extends toward the vertical Y direction in order to perform X-ray CT for subject S in the standing position.

The lower column 29 is a structure for supporting the upper column 27 slidably in a longitudinal direction D2 of the lower column 29. More specifically, the upper column 27 is supported by the lower column 29 to maintain its vertical position. The lower column 29 is shaped like a pillar such as a cylinder and a prism. The lower column 29 is placed on the floor surface to maintain its vertical position. The lower column 29 is formed of an arbitrary material such as plastic and metal. The lower column 29 has a rigid structure to support the upper column 27 and the gantry body 11. Furthermore, the lower column 29 is shaped to store the upper column 27 in order to guide the upper column 27 structurally. For example, the lower column 29 can be shaped like letter "U" as shown in FIGS. 2 and 3 to guide three sides of the prismatic upper column 27 mechanically or may have a concave portion formed in the vertical Y direction to guide four sides of the upper column 27 mechanically. The upper column 27 and lower column 29 are so located that their longitudinal directions D1 and D2 coincide with each other in the Y direction.

Typically, there are two pairs of upper and lower columns 27 and 29. The upper and lower columns 27 and 29 of one of the two pairs are connected to one side of the gantry body 11 in the X direction, and the upper and lower columns 27 and 29 of the other pair are connected to the other side of the gantry body 11 in the X direction. However, the present embodiment is not limited to this connection. For example, one of the two pairs of upper and lower columns 27 and 29 can be connected to only one side of the gantry body 11. Furthermore, the column unit 13 is shaped like a pillar; however, the present embodiment is not limited to this shape. For example, the column unit 13 may have any shape, such as a shape of letter "U" if it can support at least one side of the gantry body.

The upper column 27 need not fix the gantry body 11 such that the central axis R1 extends toward the vertical Y direction. In other words, the upper column 27 can be configured to support the gantry body 11 rotatably around the horizontal axis R2. Specifically, the upper column 27 and the gantry body 11 are connected to each other through, e.g. bearings such that the gantry body 11 can rotate around the horizontal axis R2. Hereinafter, assume that the upper column 27 supports the gantry body 11 slidably in the longitudinal direction D1 and rotatably (tiltably) around the horizontal axis R2. Since the upper column 27 is configured to support the gantry body 11 rotatably around the horizontal axis R2, one gantry 10 makes it possible to perform both X-ray CT for subjects in the standing position as shown in FIG. 2 and X-ray CT for subjects in the lying position as shown in FIG. 4. When X-ray CT is performed for a subject in the lying position, if the upper column 27 is stored in the lower column 29, the gantry body 11 can be located at the same level as the gantry body of an ordinary X-ray CT apparatus exclusively for subjects in the lying position. Therefore, like the conventional apparatuses, the X-ray CT apparatus and gantry 10 according to the present embodiment make it possible to perform X-ray CT for subjects in the lying position.

Furthermore, the upper column 27 not only can support the gantry body 11 such that the central axis R1 is maintained in the Y direction or the Z direction, but also may stop the gantry body 11 such that the central axis R1 is located at whatever angle with respect to the horizontal axis R2.

As shown in FIG. 1, the upper column 27 stores an motor (referred to as an upper column motor hereinafter) 31 for sliding the gantry body 11 in the Y direction and an motor (referred to as a tilt motor hereinafter) 33 for tilting the gantry body 11. The upper column motor 31 generates power to slide the gantry body 11 in the longitudinal direction D1 according to the control from motor control circuitry 35. Specifically, the upper column motor 31 is driven at a rotational speed corresponding to, e.g. the duty ratio of a drive signal from the motor control circuitry 35 to generate power. Upon receiving the power from the upper column motor 31, the upper column 27 slides the gantry body 11 in the longitudinal direction D1 of the upper column 27. The tilt motor 33 generates power to rotate the gantry body 11 around the horizontal axis R2 in response to a drive signal from the motor control circuitry 35. Specifically, the tilt motor 33 is driven at a rotational speed corresponding to, e.g. the duty ratio of a drive signal from the motor control circuitry 35 to generate power. Upon receiving the power from the tilt motor 33, the upper column 27 rotates the gantry body 11 around the horizontal axis R2. The lower column 29 stores an motor (referred to as a lower column motor hereinafter) 37 for sliding the upper column 27 in the Y direction. The lower column motor 37 generates power to slide the upper column 27 in the longitudinal direction D2 according to the control from the motor control circuitry 35. Specifically, the lower column motor 37 is driven at a rotational speed corresponding to, e.g. the duty ratio of a drive signal from the motor control circuitry 35 to generate power. Upon receiving the power from the lower column motor 37, the lower column 29 slides the upper column 27 in the longitudinal direction D2 of the lower column 29. The upper column motor 31, tilt motor 33 and lower column motor 37 are achieved by a motor such as a servo motor.

The motor control circuitry 35 controls the upper column motor 31, tilt motor 33 and lower column motor 37 according to the control from the gantry control circuitry 25. For example, the motor control circuitry 35 controls the upper column motor 31 and lower column motor 37 to raise and lower the gantry body 11 from the maximum height to the minimum height in a given range. The motor control circuitry 35 includes a processing unit (processor) such as a central processing unit (CPU) and a micro processing unit (MPU) and a storage device (memory) such as a read-only memory (ROM) and a random-access memory (RAM) as hardware resources. Furthermore, the motor control circuitry 35 can be achieved by an application specific integrated circuit (ASIC), a field programmable gate array (FPGA), a complex programmable logic device (CPLD), and a simple programmable logic device (SPLD). The processing unit fulfills the above-described functions by reading and executing the programs stored in the storage device. Instead of storing programs in the storage device, programs can be incorporated directly into a circuit of the processing unit and, in this case, the processing unit fulfills the functions by reading the programs out of the circuit.

As shown in FIG. 1, the X-ray tube 17 receives a high voltage from a high-voltage generator 39 to generate X-rays. The high-voltage generator 39 is attached to, for example, the rotation frame 21. The high-voltage generator 39 generates a high voltage, which is to be applied to the X-ray tube 17 under the control of the gantry control circuitry 25, from power supplied from a power unit (not shown) of the gantry body 11 through the slip ring. The high-voltage generator 39 and the X-ray tube 17 are connected to each other through a high-voltage cable (not shown). The high voltage generated by the high-voltage generator 39 is applied to the X-ray tube 17 through the high-voltage cable.

The X-ray detector 19 detects an X-ray that is generated from the X-ray tube 17 and transmitted through subject S. The X-ray detector 19 is loaded with a plurality of X-ray detection elements (not shown) which are arranged on a two-dimensional curved surface. Each of the X-ray detection elements detects an X-ray from the X-ray tube 17 and converts the detected X-ray into an electrical signal having a wave height value corresponding to the intensity of the X-ray. Each of the X-ray detection elements includes, for example, a scintillator and a photoelectric converter. The scintillator receives an X-ray to generate fluorescence. The photoelectric converter converts the generated fluorescence into a charge pulse. The charge pulse has a wave height value corresponding to the intensity of the x-ray. As the photoelectric converter, a device that converts photons into electrical signals, such as a photomultiplier and a photodiode is used. The X-ray detector 19 according to the present embodiment is not limited to an indirect-detection type detector which converts an X-ray into fluorescence first and then an electrical signal, but may be a direct-detection type detector which converts an X-ray directly into an electrical signal.

Data acquisition circuitry 41 collects digital data indicative of the intensity of X-rays reduced by subject S for each view. The data acquisition circuitry 41 is achieved by, for example, a semiconductor integrated circuit in which an integration circuit provided for each of the X-ray detection elements and an A/D converter are implemented in parallel. The data acquisition circuitry 41 is connected to the X-ray detector 19 in the gantry body 11. The integration circuit integrates electrical signals from the X-ray detection elements for a predetermined view period to generate integration signals. The A/D converter converts the integration signals into digital data having a data value corresponding to the wave height value of the integration signals. The digital data is called raw data. The raw data is a set of channel numbers and row numbers of the X-ray detection elements and digital values of X-ray intensity identified by view numbers indicative of the acquired views. For example, the raw data is supplied to the console 50 through a non-contact data transmission unit (not shown) stored in the gantry body 11.

The gantry body 11 may store not only the foregoing X-ray tube 17, X-ray detector 19, rotation frame 21, main frame, power unit, high-voltage generator 39 and data acquisition circuitry 41 but also other different devices necessary for CT. For example, a cooling unit for cooling the X-ray tube can be attached to the rotation frame 21. Furthermore, a fan for air conditioning can be attached to the gantry body 11.

The gantry control circuitry 25 controls the high-voltage generator 39, rotation motor 23 and motor control circuitry 35 according to the control from system control circuitry 61. The gantry control circuitry 25 includes a processing unit (processor) such as a CPU and an MPU and a storage device (memory) such as a ROM and a RAM as hardware resources. The gantry control circuitry 25 can be achieved by an ASIC, an FPGA, a CPLD, an SPLD or the like. The processing unit fulfills the foregoing functions by reading an executing the programs stored in the storage device. Instead of storing programs in the storage device, programs can be incorporated directly into a circuit of the processing unit and, in this case, the processing unit fulfills the functions by reading the programs out of the circuit.

The motor control circuitry 35 and the gantry control circuitry 25 can be implemented on separate substrates or a single substrate. Furthermore, the motor control circuitry 35 and the gantry control circuitry 25 can be provided at the column unit 13 of the gantry body 11 or at the console 50. If the motor control circuitry 35 is closer to the upper column motor 31, tilt motor 33 and lower column motor 37, noise due to the motor control circuitry 35 can be lowered. To reduce the noise, therefore, it is favorable that the motor control circuitry 35 be stored in the column unit 13, or the upper column 27 or the lower column 29. However, when the motor control circuitry 35 is stored in the column unit 13, the column unit 13 increases in volume. To prevent the column unit 13 from increasing in volume, therefore, the motor control circuitry 35 can be stored in a device other than the column unit 13, such as the console 50 and a dedicated device. The motor control circuitry 35 and the gantry control circuitry 25 need not be provided in a single device but can be provided in different devices.

As shown in FIG. 1, the console 50 includes an image reconstruction device 51, an image processing device 53, a display device 55, an input device 57, main storage circuitry 59 and system control circuitry 61, which are connected through a bus. Data communications between the image reconstruction device 51, image processing device 53, display device 55, input device 57, main storage circuitry 59 and system control circuitry 61 are carried out through a bus.

The image reconstruction device 51 reconstructs a CT image of subject S on the basis of raw data from the console 50. Specifically, the image reconstruction device 51 includes a pre-processing unit 511, a projection data storage unit 513 and a reconstruction unit 515. The pre-processing unit 511 pre-processes raw data from the gantry 10. The pre-processing includes various correction processes such as logarithmic conversion, X-ray intensity correction, and offset correction. The pre-processed raw data is called projection data.

The projection data storage unit 513 is a storage device, such as an HDD, an SSD and an integrated circuit storage device, which stores the projection data generated by the pre-processing unit 511. The reconstruction unit 515 generates a CT image that represents the spatial distribution of CT values regarding subject S on the basis of the projection data. As image reconstruction algorithms, the existing image reconstruction algorithm, such as an analytic image reconstruction method such as a filtered back projection (FBP) method and a convolution back projection (CBP) method and a statistic image reconstruction method such as a maximum likelihood expectation maximization (ML-EM) method and an ordered subset expectation maximization (OS-EM) method, has only to be used.

The image reconstruction device 51 includes a processing unit (processor) such as a CPU and an MPU and a storage device (memory) such as a ROM and a RAM as hardware resources. The image reconstruction device 51 can be achieved by an ASIC, an FPGA, a CPLD or an SPLD. The processing unit fulfills the functions of the pre-processing unit 511 and reconstruction unit 515 by reading and executing the programs stored in the storage device. Instead of storing programs in the storage device, programs can be incorporated directly into a circuit of the processing unit and, in this case, the processing unit fulfills the functions of the pre-processing unit 511 and reconstruction unit 515 by reading the programs out of the circuit. Furthermore, a dedicated hardware circuit serving as the pre-processing unit 511 and a dedicated hardware circuit serving as the reconstruction unit 515 can be implemented on the image reconstruction device.

The image processing device 53 performs various types of image processing for the CT image reconstructed by the image reconstruction device 51. For example, when the CT image is volume data, the image processing device 53 produces a display image by subjecting three-dimensional image processing, such as volume rendering, surface volume rendering, pixel value projection processing, multi-planar reconstruction (MPR) processing and curved planar reconstruction (CPR: curved MPR) processing, for the CT image. The image processing device 53 includes a processing unit (processor) such as a CPU and an MPU and a storage device (memory) such as a ROM and a RAM as hardware resources. The image processing device 53 can be achieved by an ASIC, an FPGA, a CPLD or an SPLD.

The display device 55 displays various items of information such as two-dimensional CT images and display images. As the display device 55, for example, a CRT display, a liquid crystal display, an organic EL display, an LED display, a plasma display, and any other displays known in the technical field of this embodiment can be used as appropriate.

The input device 57 receives various instructions and information from a user. As the input device 57, a keyboard, a mouse and various switches can be used. The input device 57 can be provided at the console 50 or the gantry 10.

The main storage circuitry 59 is a storage device, such as an HDD, an SSD and an integrated circuit storage device, for storing various items of information. The main storage circuitry 59 may be, for example, a drive device that reads and writes various information items from and to a portable storage medium such as a CD-ROM drive, a DVD drive and a flash memory. For example, the main storage circuitry 59 stores, e.g. control programs regarding the CT according to the present embodiment.

The system control circuitry 61 includes the foregoing processing unit and storage device as hardware resources.

The system control circuitry 61 functions as the center of the X-ray CT apparatus according to the present embodiment. Specifically, the system control circuitry 61 reads control programs out of the main storage circuitry 59 and expands them on the main storage circuitry 59 to control each of the units and devices of the X-ray CT apparatus in accordance with the expanded control programs.

The image reconstruction device 51, image processing device 53 and system control circuitry 61 can be integrated on a single substrate or implemented on their separate substrates.

The X-ray CT apparatus according to the present embodiment will be described in detail below.

FIG. 5 is a cross-sectional view of the gantry 10. Note that the inside of the gantry body 11 is not shown. FIG. 5 shows only one of the combinations of the upper and lower columns 27 and 29 of the gantry 10, but the other combination thereof has the same structure.

As shown in FIG. 5, the upper column 27 has a housing (referred to as an upper column housing hereinafter) 71, and the housing 71 stores a slide actuator (referred to as an upper slide actuator hereinafter) 73 for sliding the gantry body 11 in the longitudinal direction D1. The upper slide actuator 73 is achieved by, for example, a ball screw. In other words, the upper slide actuator 73 includes a screw shaft 731 and a slider 733. The screw shaft 731 is disposed in the upper column housing 71 such that its shaft center is parallel to the longitudinal direction D1. One end of the screw shaft 731 is supported rotatably by a support 75. For example, the support 75 is provided at one end of the upper column housing 71. The other end of the screw shaft 731 is connected to the upper column motor (motor) 31. The upper column motor 31 is provided at the other end of the upper column housing 71 which is opposed to the support 75. For example, as shown in FIG. 5, the support 75 is provided in the lower portion of the upper column housing 71 and the upper column motor 31 is provided in the upper portion of the upper column housing 71. However, the relationship in location between the support 75 and the upper column motor 31 is not limited to the above, but, for example, the support 75 can be provided in the upper portion of the upper column housing 71 and the upper column motor 31 can be provided in the lower portion of the upper column housing 71. The slider 733 has a through hole with a screw groove (female screw) in which a screw groove (male screw) of the screw shaft 731 is screwed. The slider 733 is screwed into the screw shaft 731. The screw shaft 731 rotates in conjunction with the rotation of the upper column motor 31 on its rotation axis, and the slider 733 slides along the direction (i.e. longitudinal direction D1) of the shaft center of the screw shaft 731 as the screw shaft 731 rotates.

A tilt actuator 77 is attached to the slider 733 of the slide actuator 73 to support the gantry body 11 rotatably around the horizontal axis R2. The tilt actuator 77 is achieved by, for example, a shaft member. The shaft member (tilt actuator) 77 is provided in the slider 733 such that its shaft center coincides with the horizontal axis. The shaft member 77 can be attached to the slider 733 directly by, e.g. a fastening or through the existing mechanical element. One end of the shaft member 77 is connected to the tilt motor (motor) 33. The tilt motor 33 is provided at, for example, the slider 733. The shaft member 77 rotates in conjunction with the rotation of the tilt motor 33 on its rotation axis. The tilt motor 33 and the shaft member 77 are directly connected to each other, but the present embodiment is not limited to this connection. For example, they can be connected indirectly through a mechanical element such as gears. The tilt motor 33 is provided at the slider 733, but the present embodiment is not limited to this. If the tilt motor 33 is connected to the shaft member 77 directly or indirectly, it can be provided in any place of the upper column housing 71. The upper column housing 71 includes a slit 79 (shown in FIGS. 2, 3 and 4) which is formed along the longitudinal direction D1 such that the shaft member 77 can slide in the longitudinal direction D1 in conjunction with the rotation of the upper column motor 31 on its rotation axis. Thus, the shaft member 77 can slide in the longitudinal direction D1 without mechanical interference of the upper column housing 71, etc. in conjunction with the rotation of the upper column motor 31 on its rotation axis.

As shown in FIG. 5, the lower column 29 has a housing (referred to as a lower column housing hereinafter) 81, and the lower column housing 81 stores a slide actuator (referred to as a lower slide actuator hereinafter) 83 for sliding the upper column 27 in the longitudinal direction D2. Like the upper slide actuator 73, the lower slide actuator 83 is achieved by, for example, a ball screw. In other words, the lower slide actuator 83 includes a screw shaft 831 and a slider 833. The screw shaft 831 is disposed in the lower column housing 81 such that its shaft center is parallel to the longitudinal direction D2. One end of the screw shaft 831 is supported rotatably by a support 85. For example, the support 85 is provided at one end of the lower column housing 81. The other end of the screw shaft 831 is connected to the lower column motor (motor) 37. The lower column motor 37 is provided at the other end of the lower column housing 81 which is opposed to the support 85. For example, as shown in FIG. 5, the support 85 is provided in the lower portion of the lower column housing 81 and the lower column motor 37 is provided in the upper portion of the lower column housing 81. However, the relationship in location between the support 85 and the lower column motor 37 is not limited to the above, but, for example, the support 85 can be provided in the upper portion of the lower column housing 81 and the lower column motor 37 can be provided in the lower portion of the lower column housing 81.

The slider 831 has a through hole with a screw groove (female screw) in which a screw groove (male screw) of the screw shaft is screwed. The slider 831 has a connecting portion 831z with the upper column 27, and the connecting portion 831z extends from the lower column housing 81 and is connected to the upper column housing 71. Specifically, the connecting portion 831z and the upper column housing 71 can be connected to each other in a whatever fashion if they are connected firmly. For example, they can be connected by a fastening such as a screw, a weld, or the combination of the fastening and weld. Furthermore, it is good that the connecting portion 831z is connected to the lower part of the upper column housing 71 to cover the lower part of the upper column housing 71. The slider 831 is screwed into the screw shaft 833. The screw shaft 833 rotates in conjunction with the rotation of the lower column motor 37 on its rotation axis. The slider 831 slides along the direction (i.e. longitudinal direction D2) of the shaft center of the screw shaft 833 as the screw shaft 833 rotates. The lower column housing 81 includes a slit (not shown) which is formed along the longitudinal direction D2 such that the connection portion 831z can slide in the longitudinal direction D2 in conjunction with the rotation of the lower column motor 37 on its rotation axis. Thus, the connecting portion 831z can slide in the longitudinal direction D2 in conjunction with the rotation of the lower column motor 31 on its rotation axis.

To slide the upper column 27 with efficiency, a guide rail (not shown) for guiding the upper column 27 to slide in the longitudinal direction D1 by the lower slide actuator 83 can be provided at the lower column housing 81 or the like. Furthermore, when the lower column housing 81 is shaped to be fitted to the upper column housing 71, the guide rail need not be provided because the lower column housing 81 is able to guide the upper column housing 71 structurally.

The ball screws of the upper and lower slide actuators 73 and 83 can be designed to have the same lead pitch or different lead pitches. The upper and lower column motors 31 and 37 can be designed to have the same motor capacity or different motor capacities.

The upper and lower columns 27 and 29 can be designed to have the same length or different lengths in the longitudinal directions D1 and D2. When they are designed to have the same length, the gantry body 11 can be raised or lowered the most efficiently.

The upper and lower slide actuators 73 and 83 are each achieved by a ball screw as described above; however, the present embodiment is not limited to this. For example, the upper and lower slide actuators 73 and 83 can be achieved by any slide actuator such as a slide rail.

The foregoing structure of the gantry 10 is one example, and the present embodiment is not limited to this example. As described above, the upper and lower columns 27 and 29 are each provided with a ball screw in the gantry 10. However, they need not be provided with a ball screw, but for example, only the upper column 27 can be provided with a ball screw. A gantry 10-2 having this structure will be describe below.

Figure 6:
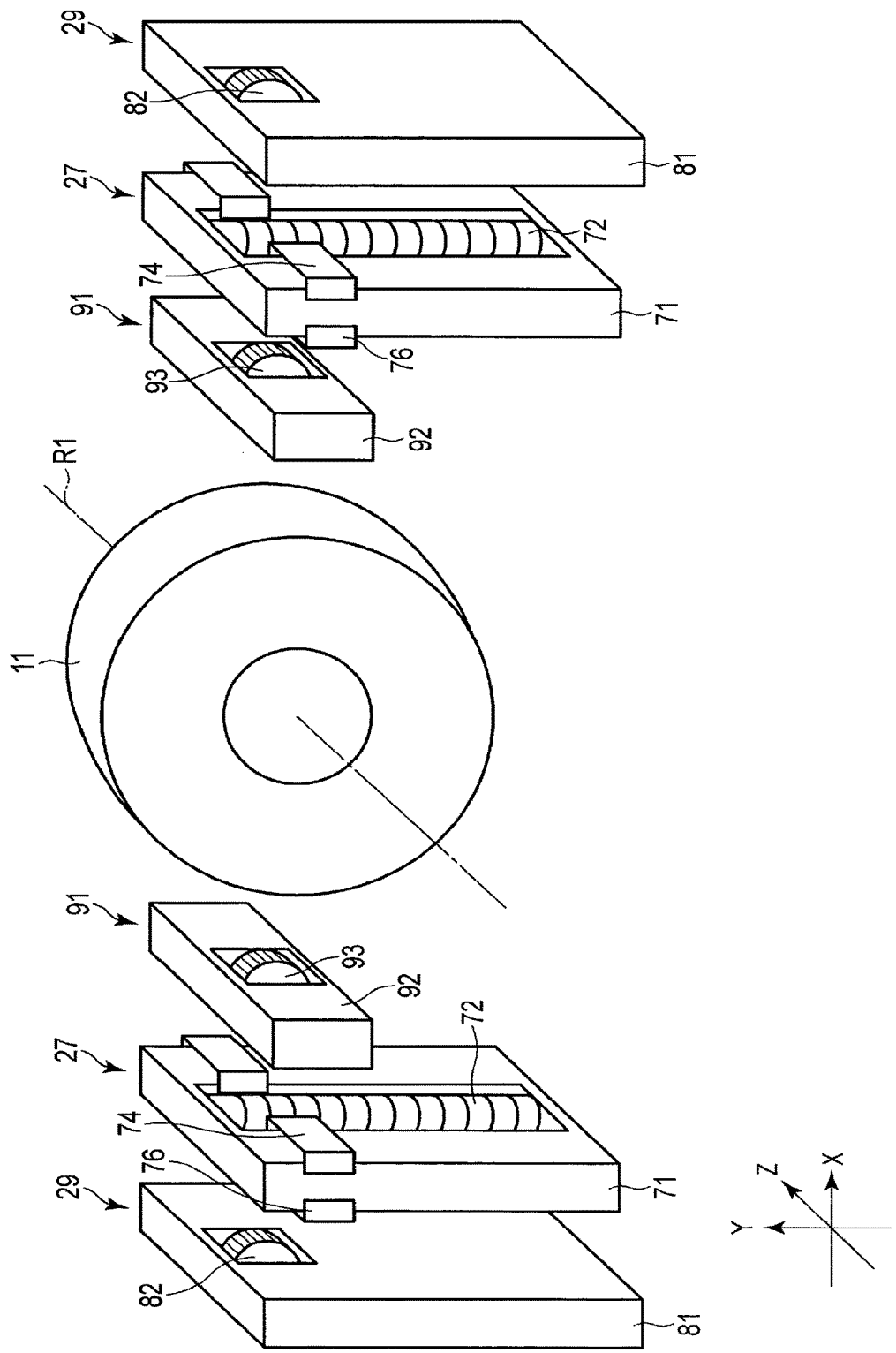
FIG. 6 is an exploded perspective view of the gantry having another structure according to the present embodiment.
Figure 7:
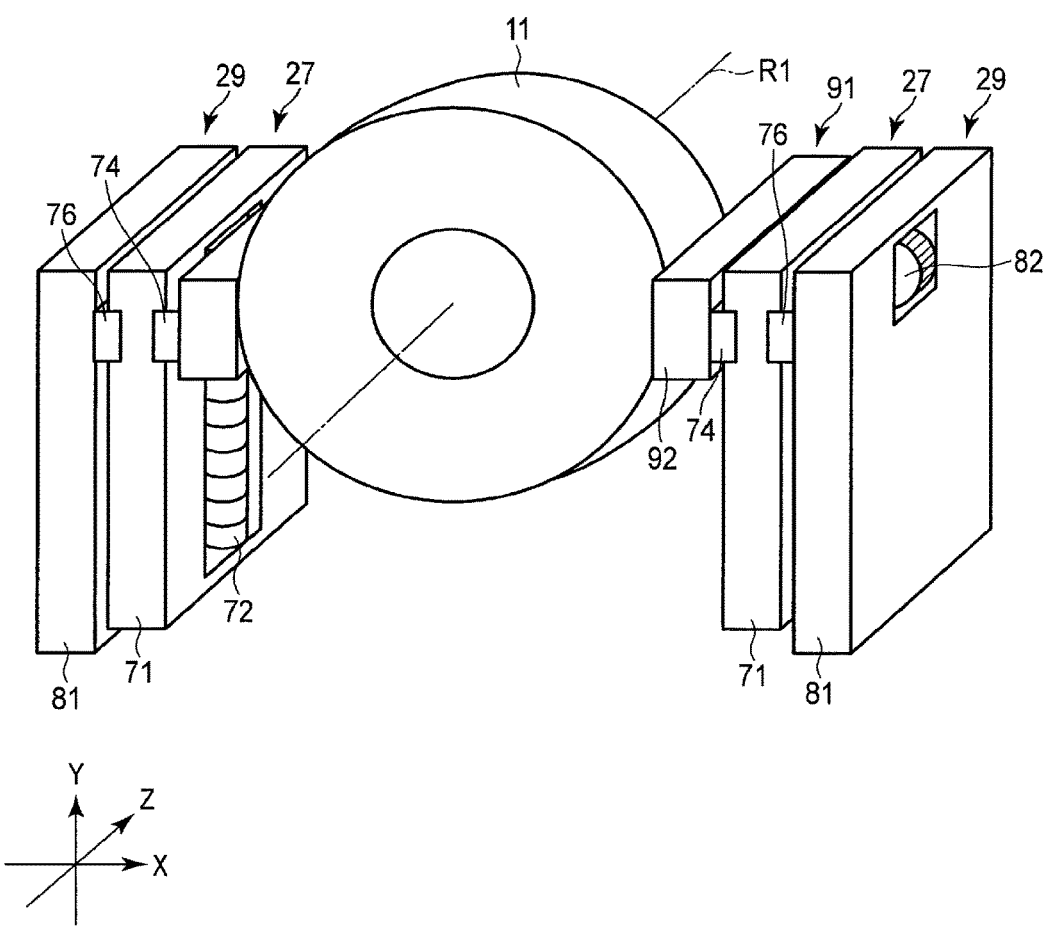
FIG. 7 is a perspective view of the gantry shown in FIG. 6.

FIG. 6 is an exploded perspective view of a gantry 10-2 having another structure according to the present embodiment. FIG. 7 is a perspective view of the gantry 10-2 shown in FIG. 6. As shown in FIGS. 6 and 7, the gantry 10-2 includes a gantry link unit 91, an upper column 27 and a lower column 29. The gantry link unit 91 is a structure for connecting a gantry body 91 and the upper column 27. The gantry link unit 91 includes a frame body 92. The frame body 92 is a frame made of, e.g. metal having a gear 93. The gantry body 91 and the upper column 27 are attached to the frame body 92. The gear 93 is a mechanical element including a number of teeth formed on the outer surface of a cylindrical body. The gear 93 is attached to the frame body 92 such that the teeth are exposed from the frame body 92. The gear 93 is engaged with a screw 72 of the upper column 27 as will be described later. Upon receiving power from an upper column motor 31 (not shown), the gear 93 rotates.

As shown in FIGS. 6 and 7, the lower column 29 includes a lower column housing 81. The lower column housing 81 is provided with a gear 82. The gear 82 is a mechanical element having a number of teeth formed on the outer surface of a cylindrical body. The gear 82 is attached to the lower column housing 81 such that the teeth are exposed from the lower column housing 81. The gear 82 is engaged with a screw 72 of the lower column 29 as will be described later. Upon receiving power from a lower column motor 37 (not shown), the gear 82 rotates.

As shown in FIGS. 6 and 7, the upper column 27 includes an upper column housing 71. The upper column housing 71 is shaped like a frame and includes a screw 72, a first linear-motion guide 74 and a second linear-motion guide 76. The screw 72 is a mechanical element which is provided along the longitudinal axis of the upper column housing 71 in the opening of the upper column housing 71 and has a helical groove formed on the surface of a cylindrical body. The screw 72 is provided such that its longitudinal axis is parallel to the Y axis, or it is toward the vertical direction. The screw 72 is attached to the upper column housing 71 such that the groove is exposed from the upper column housing 71. The screw 72 is engaged with the gear 93 of the gantry link unit 91 and the gear 82 of the lower column 29. As the screw 72, any screw can be used, but it is desirable to use a high-strength trapezoidal screw in which a trapezoidal thread is formed.

As shown in FIGS. 6 and 7, the frame body 92 of the gantry link unit 91 is attached to the first linear-motion guide 74. Specifically, the first linear-motion guide 74 includes a rail (not shown) formed along the longitudinal axis of the screw 72 and a block slidably attached to the rail. The frame body 92 is attached to the block. The lower column housing 81 of the lower column 29 is attached to the second linear-motion guide 76. Specifically, the second linear-motion guide 76 includes a rail (not shown) formed along the longitudinal axis of the screw 72 and a block slidably attached to the rail. The lower column housing 81 is attached to the block. The first and second linear-motion guides 74 and 76 are slidably provided at the upper column housing 71 separately from each other.

When an instruction to raise the upper column 27 is input by the input device 57 or the like, the gear 82 is engaged with the screw 72 and rotated in the forward direction by the lower column motor 37 (not shown), and the upper column 27 is slid upward by the second linear-motion guide 76. When an instruction to raise the gantry link unit 91 is input by the input device 57 or the like, the gear 93 is engaged with the screw 72 and rotated in the forward direction by the upper column motor 31 (not shown), and the gantry link unit 91 is slid upward by the first linear-motion guide 74. When an instruction to lower the upper column 27 is input by the input device 57 or the like, the gear 82 is engaged with the screw 72 and rotated in the backward direction by the lower column motor 37 (not shown), and the upper column 27 is slid downward by the second linear-motion guide 76. When an instruction to lower the gantry link unit 91 is input by the input device 57 or the like, the gear 93 is engaged with the screw 72 and rotated in the backward direction by the upper column motor 31 (not shown), and the gantry link unit 91 is slid downward by the first linear-motion guide 74.

The number of gears 93 provided at the gantry link unit 91 is not limited to one. A plurality of gears 93 can be provided at the gantry link unit 91 according to design. Similarly, the number of gears 82 provided at the lower column 29 is not limited to one, but a plurality of gears 82 can be provided at the lower column 29 according to design.

Figure 8:
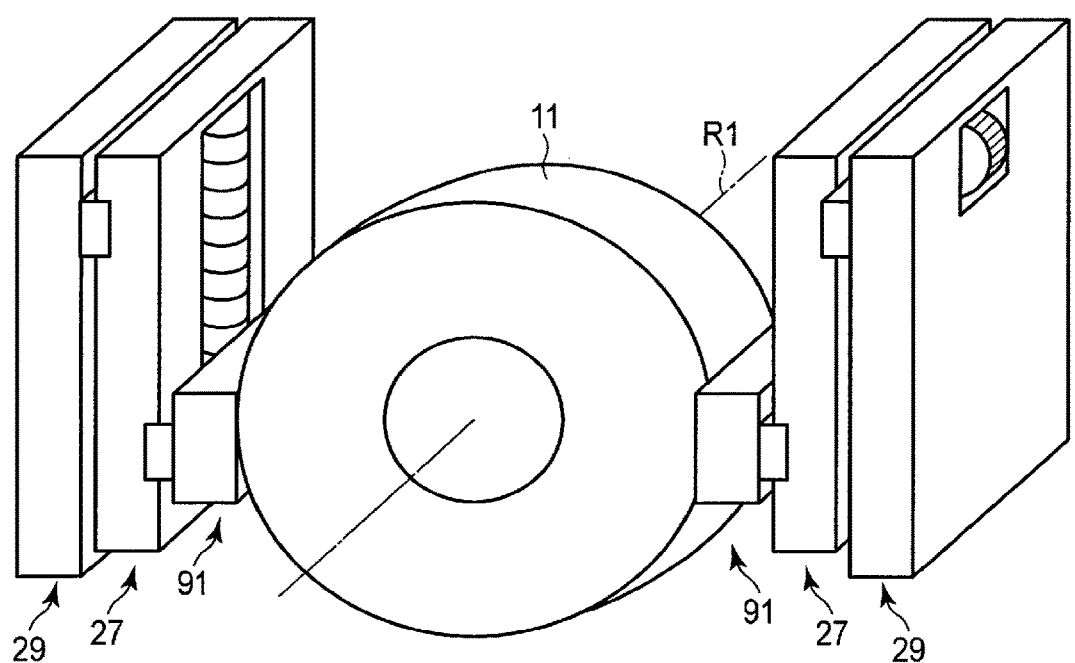
FIG. 8 is a perspective view of the gantry shown in FIG. 6, the gantry body of which is located at the minimum height.
Figure 9:
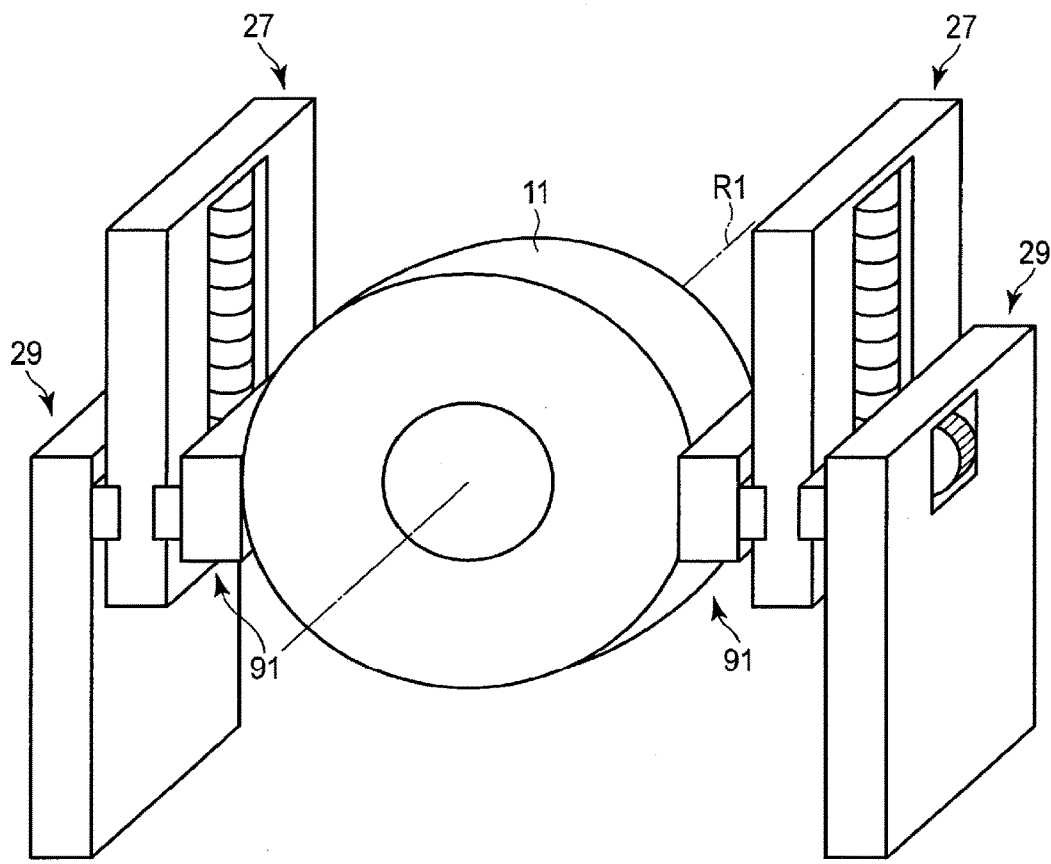
FIG. 9 is a perspective view of the gantry shown in FIG. 6, the gantry body of which is located at the middle height.

FIG. 8 is a perspective view of a gantry 10-2, the gantry body 11 of which is located at the minimum position. FIG. 9 is a perspective view of the gantry 10-2, the gantry body 11 of which is located at the middle between the maximum and minimum heights. FIG. 10 is a perspective view of the gantry 10-2, the gantry body of which is located at the maximum height. The minimum height is the height of the gantry body 11 when the gantry link unit 91 is located at the lower limit of a movable range of the second linear-motion guide 76 and when the upper column 27 is located at the upper limit of a movable range of the first linear-motion guide 74. The middle height is a height of the gantry body 11 when the gantry link unit 91 is located at the lower limit of the movable range of the second linear-motion guide 76 and when the upper column 27 is located at the lower limit of the movable range of the first linear-motion guide 74. The maximum height is the height of the gantry body 11 when the gantry link unit 91 is located at the upper limit of the movable range of the second linear-motion guide 76 and when the upper column 27 is located at the lower limit of the movable range of the first linear-motion guide 74. As shown in FIG. 7, the middle height can be defined as a height of the gantry body 11 when the gantry link unit 91 is located at the upper limit of the movable range of the second linear-motion guide 76 and when the upper column 27 is located at the upper limit of the movable range of the first linear-motion guide 74.

As shown in FIGS. 8, 9 and 10, even in the structure of the gantry 10-2, the gantry body 11 can be located in an arbitrary position between the maximum height and the minimum height by driving the gear 93 provided at the gantry link unit 91 and the gear 82 provided at the lower column 29.

When the gantry body 11 is raised or lowered, the upper column motor 31 and the lower column motor 37 can be driven in an arbitrary order. An example where the gantry body 11 is raised from the minimum height in FIG. 8 to the maximum height in FIG. 10 will be described. As a first method of the example, the motor control circuitry 35 first drives the lower column motor 37 to raise the gantry body 11 from the minimum height in FIG. 8 to the middle height in FIG. 9 and then drives the upper column motor 31 to raise the gantry body 11 from the middle height in FIG. 9 to the maximum height in FIG. 10. As a second method of the example, the motor control circuitry 35 first drives the upper column motor 31 to raise the gantry body 11 from the minimum height in FIG. 8 to the middle height in FIG. 9 and then drives the lower column motor 37 to raise the gantry body 11 from the middle height in FIG. 9 to the maximum height in FIG. 10.

The same as above is true of an example where the gantry body 11 is lowered from the maximum height in FIG. 10 to the minimum height in FIG. 8. In other words, the gantry body 11 can be moved from the maximum height in FIG. 10 to the minimum height in FIG. 8 through the middle height in FIG. 9.

As described above, in the gantry 10-2 according to the present embodiment, the screw 72 is formed only in the upper column 27. Thus, the gantry 10-2 can take up less space than the case where the ball screw is provided in each of the upper and lower columns 27 and 29. Since, furthermore, the upper and lower columns 27 and 29 can be moved by a single screw 72, the gantry 10-2 can ensure higher accuracy than a case where a plurality of screws are required.

An example of operation of the gantries 10 and 10-2 according to the present embodiment will be described in detail below. The following example of operation is common to both the gantries 10 and 10-2. The gantry 10 will be described below as the example unless otherwise specified in particular.

Figure 11:
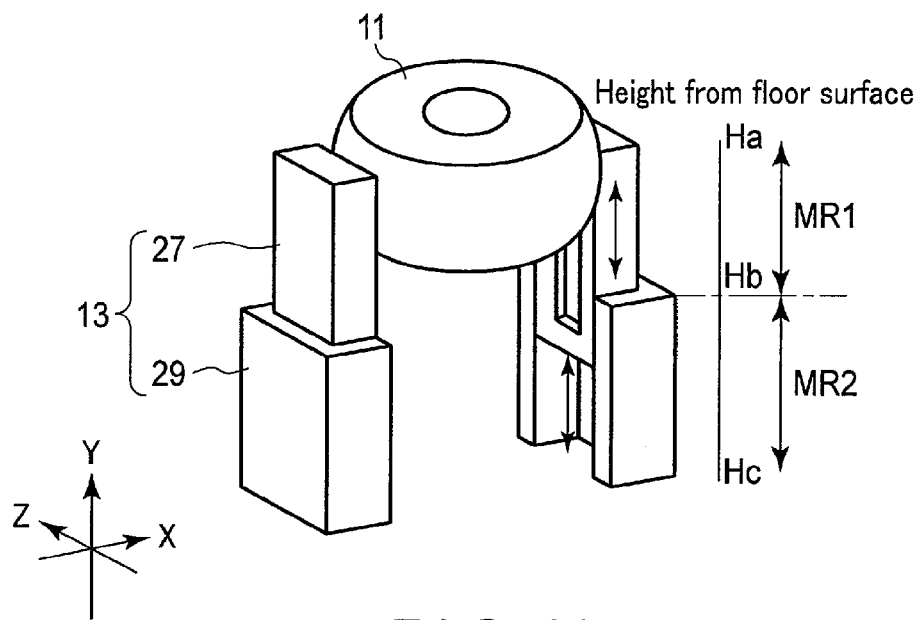
FIG. 11 is an external view of the gantry according to the present embodiment, in which the gantry body is located at the maximum height in a movable range of the gantry.
Figure 12:
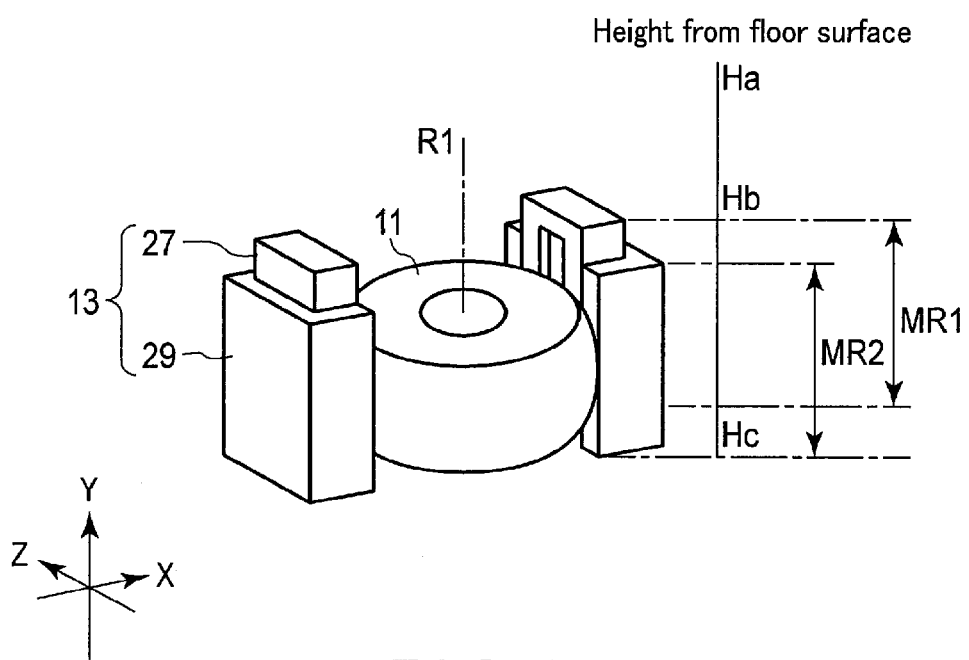
FIG. 12 is an external view of the gantry according to the present embodiment, in which the gantry body is located at the minimum height in a movable range of the gantry.

FIG. 11 is an external view of the gantry 10 according to the present embodiment, in which the gantry body is located at the maximum height in a movable range of the gantry body 11. FIG. 12 is an external view of the gantry 10 according to the present embodiment, in which the gantry body 11 is located at the minimum height in a movable range of the gantry body 11. As shown in FIGS. 11 and 12, the upper column 27 supports the gantry body 11 slidably in the longitudinal direction D1, and the lower column 29 supports the upper column 27 slidably in the longitudinal direction D2. With this structure, the motor control circuitry 35 can control the upper and lower column motors 31 and 37 to slide the upper column 27 upward in the vertical direction with respect to the lower column 29 to extend the column unit 13 and to slide the upper column 27 downward in the vertical direction with respect to the lower column 29 to contract the column unit 13.

The movable range MR1 of the gantry body 11 in the longitudinal direction D1 by the upper column 27 corresponds to the movable range of the slider 733 by the upper slide actuator 73. The movable range MR2 of the upper column 27 in the longitudinal direction D2 by the lower column 29 corresponds to the movable range of the slider 833 by the lower slide actuator 83. Here, the height of the gantry body 11 from the floor surface in the case where the gantry body 11 is located at the upper limit of the movable range MR1 and the upper column 27 is located at the upper limit of the movable range MR2, is defined as a maximum height Ha, and the height of the gantry body 11 from the floor surface when the gantry body 11 is located at the lower limit of the movable range MR1 and the upper column 27 is located at the lower limit of the movable range MR2 is defined as a minimum height Hc. Furthermore, the height of the gantry body 11 from the floor surface when the gantry body 11 is located at the upper limit of the movable range MR1 and the upper column 27 is located at the lower limit of the movable range MR2 is defined as a middle height Hb. Note that the height of the gantry body 11 from the floor surface is the height of the horizontal axis R2 of the gantry body 11 from the floor surface.

The imaging range of X-ray CT is set in an arbitrary range between the maximum height Ha and the minimum height Hc by the gantry control circuitry 25, the system control circuitry 61, etc. The imaging range can be set to an arbitrary value by the input device 57 or automatically set in accordance with, e.g. a portion to be imaged and an imaging mode by the gantry control circuitry 25, the system control circuitry 61, etc.

In order to raise and lower the gantry body 11 within the imaging range, the motor control circuitry 35 controls the upper and lower column motors 31 and 37 in synchronization with each other. The mode in which the motor control circuitry 35 controls the upper and lower column motors 31 and 37 can be divided into a whole-body imaging mode and a partial imaging mode from the viewpoint of the imaging range.

Typically, the whole-body imaging mode is a mode in which X-ray CT is performed for the whole body of subject S while raising or lowering the gantry body 11. The imaging range of the whole-body imaging mode is set in a range that is wider than one of the movable ranges MR1 and MR2. When the imaging range is wider than the movable range MR1 or movable range MR2, the motor control circuitry 35 drives the upper and lower column motors 31 and 37 in sequence to raise or lower the gantry body 11.

The partial imaging mode is a mode in which X-ray CT is performed for part of subject S while the gantry body 11 is being raised or lowered or it is fixed at a given height. The imaging range of the partial imaging mode is set in a range that is narrower than one of the movable ranges MR1 and MR2. When the imaging range is included in the movable range MR1, the motor control circuitry 35 drives the upper column motor 31 to raise or lower the gantry body 11.

The above-described control mode can be divided into an individual drive mode and a simultaneous drive mode from the viewpoint of the speed at which the gantry body 11 is raised or lowered. The individual drive mode is a mode in which one of the upper and lower column motors 31 and 37 is selected and driven. The simultaneous drive mode is a mode in which the upper and lower column motors 31 and 37 are driven simultaneously in order to raise or lower the gantry body 11 at a speed that is higher than in the individual drive mode.

An example of operation of the gantry 10 will be described below for each of the whole-body imaging mode and the partial imaging mode.

EXAMPLE 1

The whole-body imaging mode will be described below.

In the preparation stage of whole-body imaging, the gantry body 11 is located at the imaging start position. A subject S stands in a passage of the bore 15 of the gantry body 11. When preparations are completed, a user gives an instruction to image the whole body of subject S by, e.g. the input device 57. When the gantry control circuitry 25 receives the instruction, it controls the high-voltage generator 39, the rotation motor 23 and the motor control circuitry 35 synchronously to image the whole body of subject S. More specifically, the gantry control circuitry 25 controls the rotation motor 23 to rotate the rotation frame 21 around the central axis R1, controls the motor control circuitry 35 to raise or lower the gantry body 11 in the imaging range, and controls the high-voltage generator 39 to generate X-rays from the X-ray tube 17 while the rotation frame 21 is rotating and the gantry body 11 is rising or lowering. The X-rays generated from the X-ray tube 17 is transmitted through subject S and detected by the X-ray detector 19. The data acquisition circuitry 41 collects raw data corresponding to the X-rays detected by the X-ray detector 19. The collected raw data is transmitted to the image reconstruction device 51 by a non-contact data transmission device. The image reconstruction device 51 reconstructs volume data about the whole body of subject S on the basis of the raw data. The reconstructed volume data is converted into a two-dimensional display image by the image processing device 53, and the display image is displayed on the display device 55.

The raising and lowering of the gantry body 11 to the imaging start position can be performed in response to an instruction that a user gives by manually operating the input device 57 or it can be done automatically according to an operation sequence for positioning the gantry body in the imaging start position (referred to as a positioning sequence hereinafter).

When it is performed manually, the user gives an instruction to raise or lower the gantry body 11 through the input device 57 that is provided in the console 50 or the gantry 10. The motor control circuitry 35 drives the upper column motor 31 and the lower column motor 37 in sequence to raise or lower the gantry body 11 in a direction corresponding to the instruction to raise or lower the gantry body. When the user gives an instruction to raise or lower the gantry body 11 through the input device 57 provided in the gantry 10, the user need not go to a control room each time the instruction is provided, with the result that user's effort can be reduced. When the instruction is given through the input device 57 provided in the console 50, user's safety can be ensured.

When it is performed automatically, the motor control circuitry 35 receives an instruction to start to image the whole body of a subject through the input device 57 by the user and drives the upper column motor 31 and the lower column motor 37 in sequence to raise or lower the gantry body 11 to a predetermined imaging position.

Hereinafter, an example of operation of the motor control circuitry 35 in whole-body imaging will be described in detail for each of the individual and simultaneous driving operations. As described above, the whole-body imaging can be performed in an arbitrary range between the maximum height Ha and the minimum height Hc if the range is wider than each of the movable ranges MR1 and MR2; however, it is assumed that the whole-body imaging can be performed in the entire range from the maximum height Ha to the minimum height He in order to give the following descriptions more specifically. The X-ray CT can be performed while the gantry body 11 is lowering or rising. When subject S is set at its imaging position, the gantry body 11 is located at the maximum height Ha; thus, time for performing X-ray CT while the gantry body 11 is lowering can be made shorter. On the other hand, if X-ray CT is performed while the gantry body 11 is rising, subject S can be prevented from being caught by the gantry body 11. To give the following descriptions more specifically, it is assumed that X-ray CT is performed while the gantry body 11 is being lowered and, in other words, the imaging start position is Ha and the imaging end position is Hc. Assume in the following descriptions that ball screws of the upper and lower slide actuators 73 and 83 are designed to have the same lead pitch and the upper and lower column motors 31 and 37 are designed to have the same motor capacity, unless otherwise specified in particular. It should be noted that even though the actuators 73 and 83 have different lead pitches and the devices 31 and 37 have different motor capacities, the control aspect of the motor control circuitry 35 does not vary.

First, the whole-body imaging in individual drive mode will be described.

Figure 14:
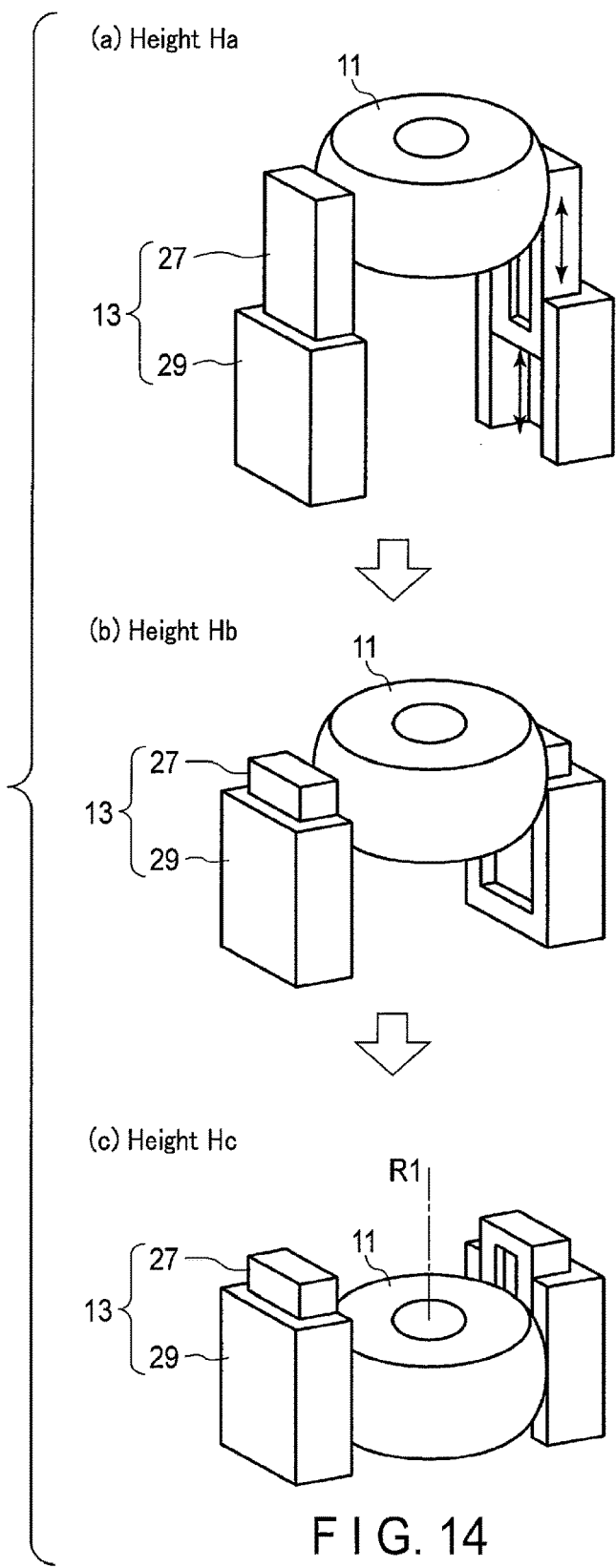
FIG. 14 is a diagram showing a process of movement of the gantry body according to the operation sequence shown in FIG. 13.

FIG. 13 is a chart showing an operation sequence in the whole-body imaging mode which is performed by the motor control circuitry 35. FIG. 14 is a diagram showing a process of movement of the gantry body 11 according to the operation sequence shown in FIG. 13. In FIG. 13, the vertical axis represents the velocity of the upper slide actuator 73, lower slide actuator 83 and gantry body 11, and the horizontal axis represents the height of the floor surface. The velocity of the lower slide actuator 73 shows the absolute velocity at which the lower slide actuator 83 slides the upper column 27, and the velocity of the gantry body 11 shows the absolute velocity at which the gantry body 11 rises or lowers. The velocity of the upper slide actuator 73 shows the absolute velocity at which the upper slide actuator 73 slides the gantry body 11, which is observed from the upper column 27. When the upper column 27 stops, the velocity of the upper slide actuator 73 is equal to the absolute velocity at which the upper slide actuator 73 slides the gantry body 11.

Upon receipt of an instruction to image the whole body of a subject, the gantry control circuitry 25 supplies the motor control circuitry 35 with an instruction signal to execute an operation sequence for the whole-body imaging (referred to as a whole-body imaging sequence hereinafter). Upon receipt of the instruction signal, the motor control circuitry 35 controls the upper and lower column motors 31 and 37 simultaneously in accordance with the whole-body imaging sequence. In the whole-body imaging sequence, the motor control circuitry 35 selects and drives one of the upper and lower column motors 31 and 37 in such a manner that the gantry body 11 lowers at a constant velocity Vcon from the maximum height Ha to the minimum height Hb. In other words, the movable range MR1 for the upper slide actuator 73 and the movable range MR2 for the lower slide actuator 83 do not overlap each other in the imaging range. While the motor control circuitry 35 is operating, it uses a position detector such as a rotary encoder and a potentiometer to monitor the height of the slider 833 of the lower slide actuator 83, or the height of the upper column 27 from the floor surface and the height of the slider 733 of the upper slide actuator 73, or the height of the gantry body 11 from the slider 733.

More specifically, as shown in FIG. 13, the motor control circuitry 35 first drives the lower column motor 37 to slide the upper column 27 along the longitudinal direction D2 by means of the lower slide actuator 83. The upper column 27 and the gantry body 11 are lowered at a given velocity Vcon by the lower column motor 37. When the upper column 27 lowers to the lower limit of the movable range MR1, or when the gantry body 11 lowers to the middle height Hb, the motor control circuitry 35 stops the lower column motor 37 and drives the upper column motor 31. Accordingly, the gantry body 11 is lowered at a given velocity Vcon by the upper column motor 31. When the gantry body 11 lowers to the lower limit of the movable range MR2, or when the gantry body 11 lowers to the minimum height Hc, the motor control circuitry 35 stops the upper column motor 31.

Furthermore, when the gantry body 11 lowers to the minimum height Hc, the gantry control circuitry 25 controls the rotation motor 23 to stop the rotation frame 21 and controls the high-voltage generator 39 to stop the X-ray tube 17 from generating X rays.

Thus, the individual drive whole-body imaging is completed. As described above, the gantry 10 is able to perform X-ray CT within a broad imaging range, which cannot be covered by the upper slide actuator 73 or lower slide actuator 83 alone, by switching between the upper and lower column motors 31 and 37. Unlike in the simultaneous drive mode for driving the upper and lower column motors 31 and 37 simultaneously, in the individual drive mode, one of the upper and lower column motors 31 and 37 is driven; thus, the velocity at which the gantry body 11 rises and lowers within each of the movable ranges MR1 and MR2, can be adjusted with high accuracy.

In the foregoing operation example, the lower column motor 37 lowers the upper column 27 first and then the upper column motor 31 lowers the gantry body 11. However, the present embodiment is not limited to this example. For example, the upper column motor 31 may lower the gantry body 11 and then the lower column motor 37 may lower the upper column 27.

In the foregoing individual drive, when the upper column 27 reaches the lower limit of the movable range MR2 of the lower slide actuator 83 (in the above example, for example, when the gantry body reaches the middle height Hb), the lower column motor 37 is switched to the upper column motor 31. If the lower column motor 37 is not switched to the upper column motor 31 instantaneously, it is likely that the velocity of the gantry body 11 will be varied at the middle height Hb.

FIG. 15 is a chart showing another operation sequence in the whole-body imaging mode which is performed by the motor control circuitry 35. This operation sequence is performed in order to reduce the variations in velocity due to switching from the lower column motor 37 to the upper column motor 31.

To reduce the variations in velocity due to switching from the lower column motor 37 to the upper column motor 31, the motor control circuitry 35 includes the height (middle height Hb) of the gantry body 11 from the floor surface when the gantry body 11 is located at the upper limit of the movable range MR1 of the upper slide actuator 73 and the upper column 27 is located at the lower limit of the movable range MR2 of the lower slide actuator 83, and gradually switches between the lower and upper column motors 37 and 31 in a given range (referred to as a switching range hereinafter) 2α that is narrower than the imaging range. In other words, the movable range MR1 for the upper slide actuator 73 and the movable range MR2 for the lower slide actuator 83 overlap each other in the switching range 2α of the imaging range. In the switching range, the outputs of the lower and upper column motors 37 and 31 are so controlled that the gantry body 11 moves at the constant velocity Vcon. The switching range has only to be determined according to the performance of the lower and upper column motors 37 and 31. The switching range can be set at an arbitrary value through the input device 57 by a user.

More specifically, as shown in FIG. 15, the motor control circuitry 35 first drives the lower column motor 37 only to lower the upper column 27 and the gantry body 11 from the maximum height Ha at a given velocity Vcon. When the gantry body 11 lowers from the middle height Hb to half α the distance of the switching range, or when it lowers to a position Hb+α, the motor control circuitry 35 starts to switch from the lower column motor 37 to the upper column motor 31. The switching is completed when the upper column 27 reaches the lower limit of the movable range MR1, or before the gantry body 11 lowers to the position Hb−α. More specifically, when the gantry body 11 lowers to the position Hb+α, the motor control circuitry 35 gradually decreases the output of the lower column motor 37 to decrease the velocity of the lower slide actuator 83 from Vcon to 0 and gradually increases the output of the upper column motor 31 to accelerate the velocity of the upper slide actuator 73 from 0 to Vcon, while the gantry body 11 is lowering by the switching range 2α. In other words, the upper and lower column motors 31 and 37 are controlled synchronously such that the velocity of the upper column 27 increases and that of the lower column 29 decreases in the switching range 2α. When X-ray CT is performed while raising the gantry body 11, the upper and lower column motors 31 and 37 are controlled synchronously such that the velocity of the upper column 27 decreases and that of the lower column 29 increases in the switching range 2α. The velocity can be varied linearly or non-linearly. The outputs of the lower and upper column motors 37 and 31 can be adjusted by the duty ratio of a drive signal from the motor control circuitry 35 or by a decelerator.

When the gantry body 11 reaches a position Hb−α of the end of the switching range, the motor control circuitry 35 drives only the upper column motor 31 to lower the gantry body 11. When the gantry body 11 lowers to the lower limit of the movable range MR2 of the lower slide actuator 83, or when the gantry body 11 lowers to the minimum height Hc, the motor control circuitry 35 stops the upper column motor 31.

Thus, the individual drive whole-body imaging using the switching range 2α is completed. As described above, the switching range 2α makes it possible to switch between the upper and lower column motors 31 and 37 gradually. Thus, the gantry body 11 can be lowered at a constant velocity with high accuracy in the imaging range. This can prevent an image artifact due to the variations in velocity.

Next, the simultaneous drive whole-body imaging will be described.

Figure 16:
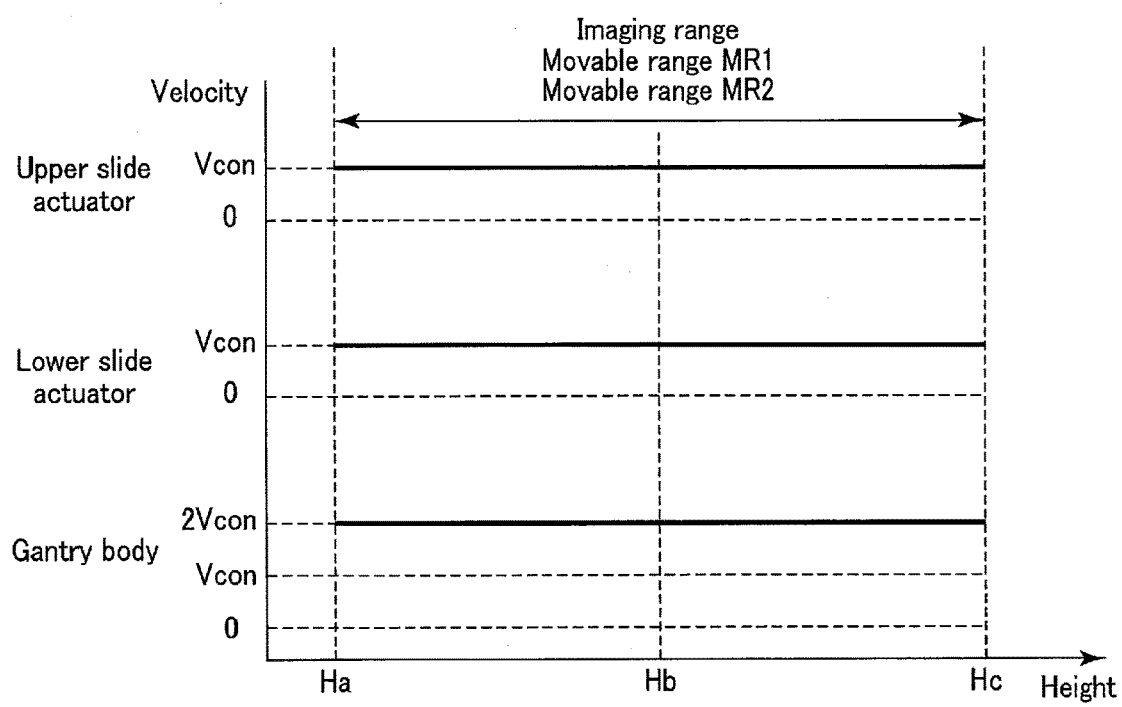
FIG. 16 is a chart showing an operation sequence in a whole-body imaging mode for simultaneous drive, which is performed by the motor control circuitry shown in FIG. 1.

FIG. 16 is a chart showing an operation sequence in a whole-body imaging mode for simultaneous drive, which is performed by the motor control circuitry 35. When the whole body of a subject is imaged in the simultaneous drive mode, the motor control circuitry 35 drives the upper and lower column motors simultaneously in such a manner that the gantry body 11 lowers at constant velocity 2Vcon from the maximum height Ha to the minimum height Hb. In other words, the movable range MR1 for the upper slide actuator 73 and the movable range MR2 for the lower slide actuator 83 overlap each other in the imaging range. The velocity 2Vcon is the sum of velocity Vcon of the upper slide actuator 73 and velocity Vcon of the lower slide actuator 83.

More specifically, as shown in FIG. 16, the motor control circuitry 35 first drives the upper and lower column motors 31 and 37 simultaneously to lower the slider 733 of the upper slide actuator 73 and the slider 833 of the lower slide actuator 83 at velocity Vcon. Accordingly, the gantry body 11 lowers at velocity 2Vcon. When the gantry body 11 lowers to the minimum height Hc, the motor control circuitry 35 stops the upper and lower column motors 31 and 37.

Therefore, simultaneous drive imaging can be performed at high velocity and imaging time can be shortened. Since imaging time for the simultaneous drive is shorter than that for the individual drive, the exposed dose of subject S is reduced.

In the foregoing descriptions, the ball screws of the upper and lower slide actuators 73 and 83 have the same lead pitch, and these actuators 73 and 83 have the same motor capacity. However, the lead pitch may vary from the upper slide actuator 73 to the lower slide actuator 83, and the motor capacity may vary from the upper slide actuator 73 to the lower slide actuator 83. If, in this case, the whole-body imaging is performed, the velocity of the gantry body 11 varies from the movable range MR1 to the movable range MR2 and thus an uneven image will be formed due to the variation in velocity. For this reason, when the whole-body imaging is performed within a range that is wider than the movable range MR1 or MR2, the motor control circuitry 35 may drive the upper and lower column motors 31 and 37 simultaneously. Since, therefore, the motor control circuitry 35 is able to raise and lower the gantry body 11 at a constant velocity in a wide imaging range, an uneven image due to a variation in velocity can be decreased.

EXAMPLE 2

Partial imaging will be described below.

As described above, the partial imaging mode is a mode in which X-ray CT is performed in a range that is narrower than one of the movable ranges MR1 and MR2. In the partial imaging mode, the gantry body 11 need not always be raised or lowered during X-ray CT depending on the imaging range. In the following descriptions, however, it is assumed that the gantry body 11 is raised and lowered. In the partial imaging mode, too, the ball screws of the upper and lower slide actuators 73 and 83 may have the same lead pitch or different lead pitches, and the upper and lower column motors 31 and 37 may have the same motor capacity or different motor capacities. In the following descriptions, however, it is assumed that the ball screws of the upper and lower slide actuators 73 and 83 have different lead pitches and the upper and lower column motors 31 and 37 have different motor capacities. More specifically, it is assumed that the lead pitch of the ball screw of the upper slide actuator 73 is longer than that of the ball screw of the lower slide actuator 83, and the motor capacity of the upper column motor 31 is larger than that of the lower column motor 37. In the following descriptions, the upper slide actuator 73 slides the upper column 27 at velocity Vhigh and the lower slide actuator 83 slides the lower column 29 at velocity Vlow. Even though the lead pitch and the motor capacity each varies, the control mode of the motor control circuitry 35 does not vary.

FIGS. 17A and B is a chart showing an operation sequence in the partial imaging mode performed by the motor control circuitry 35. In FIG. 17A, the vertical axis represents velocity and the horizontal axis represents time. In FIG. 17B, the vertical axis represents a position and the horizontal axis represents time. The upper slide actuator 73 is able to operate at velocity Vhigh and the lower slider actuator 83 is able to operate at velocity Vlow that is lower than velocity Vhigh. It is assumed that the imaging start position is height Hs and the imaging end position is height He. It is also assumed that the gantry body 11 is located at height Hc at start time Tpe of a positioning operation.

As shown in FIGS. 17A and 17B, in the partial imaging mode, the motor control circuitry 35 drives the lower column motor 37 to raise and lower the upper column 27 at a low velocity Vlow using the lower slide actuator 83, thereby performing a positioning operation. After the positioning operation is completed, the motor control circuitry 35 drives the upper column motor 31 to raise and lower the lower column 29 at a high velocity Vhigh using the upper slide actuator 73, thereby performing an imaging operation. In this positioning operation, since the gantry body 11 is raised and lowered at a low velocity Vlow, subject S can be prevented from being caught by the gantry body 11 and a subject's feeling of anxiety can be reduced. When X-ray CT is performed, since the gantry body 11 is raised or lowered at a high velocity Vhigh, the exposed dose of subject S can be decreased. Below are detailed descriptions of the partial imaging.

As shown in FIGS. 17A and 17B, when an instruction to perform a positioning operation is input through the input device 57 at time Tpe, the gantry control circuitry 25 causes the motor control circuitry 35 to start the positioning operation. In the positioning operation, the motor control circuitry 35 drives the upper column motor 31 to raise the lower column 29 at a high velocity Vhigh using the upper slide actuator 73 and locate the gantry body 11 at the imaging start position Hs. The gantry body 11 can be moved to the imaging start position Hs manually in accordance with a user's instruction using the input device 57 or automatically in accordance with a positioning sequence.

When the gantry body 11 is located at the imaging start position (time Tpe), the motor control circuitry 35 stops driving the lower column motor 37. In the partial imaging mode, it is desirable to set the imaging range such that switching need not be performed between the upper and lower column motors 31 and 37 between the imaging start position Hs and the imaging end position He. Specifically, the motor control circuitry 35 positions the gantry body 11 and the upper column 27 such that the middle height of the imaging range coincides with that of the movable range MR1 of the upper slide actuator 73.

When preparations for X-ray CT are completed, a user inputs an imaging instruction through the input device 57 (time Tss). When the imaging instruction is input, the gantry control circuitry 25 controls the high-voltage generator 39, rotation motor 23 and motor control circuitry 35 simultaneously to perform partial imaging for subject S. More specifically, the gantry control circuitry 25 controls the rotation motor 23 to rotate the rotation frame 21 around the central axis R1, and controls the motor control circuitry 35 to raise the gantry body 11 within the imaging range, and also controls the high-voltage generator 39 to generate X rays from the X-ray tube 17 while the rotation frame 21 is rotating and the gantry body 11 is rising. The X rays generated from the X-ray tube 17 is transmitted through subject S and then detected by the X-ray detector 19. The data acquisition circuitry 41 collects raw data corresponding to the X rays detected by the X-ray detector 19. The collected raw data is transmitted to the image reconstruction device 51 through the non-contact data transmission unit. The image reconstruction device 51 reconstructs volume data about an imaging portion of subject S on the basis of the raw data. The reconstructed volume data is converted to a two-dimensional display image by the image processing device 53 and displayed on the display device 55.

The imaging operation to be performed by the motor control circuitry 35 will be described specifically. When the gantry control circuitry 25 gives an imaging instruction, the motor control circuitry 35 drives the upper column motor 31 to raise the gantry body 11 at velocity Vhigh from the imaging start position Hs to the imaging end position He through the upper slide actuator 73. When the gantry body 11 reaches the imaging end position He, the motor control circuitry 35 stops the upper column motor 31.

Thus, the partial imaging is completed. In the foregoing example, the motor control circuitry 35 drives only the upper column motor 31 within the imaging range of the partial imaging; however, the present embodiment is not limited to this. In other words, the motor control circuitry 35 is able to perform high-speed imaging by driving the upper and lower column motors 31 and 37 simultaneously within the imaging range of the partial imaging. In the positioning operation, the motor control circuitry 35 drives only the lower column motor 37; however, the present embodiment is not limited to this. In other words, the upper and lower column motors 31 and 37 can be driven simultaneously to move the gantry body 11 at a high velocity if the risk that subject S may be caught by the gantry body 11 is low.

As described above, the gantry 10 allows partial imaging as well as whole-body imaging. The upper and lower slide actuators 73 and 83 can be caused to differ in their use by causing them to differ in their velocity. For example, if the upper slide actuator 73 is slid more quickly than the lower slide actuator 83, the upper slide actuator 73 can be used specifically for imaging and the lower slide actuator 83 can be used specifically for positioning. Therefore, subject S can be prevented from being caught by the gantry body 11 at the time of positioning, and the exposed dose of subject S can be reduced at the time of imaging.

Subsequent to the foregoing descriptions of an operation example of the gantry 10 according to the present embodiment, advantages of the structure of the gantry 10 will be described in detail.

To achieve X-ray CT for subjects in the standing position, the gantry body needs to rise close to the ceiling. As a gantry having such a gantry body, there is a column fixed type gantry shown in FIG. 18 and a column stored type gantry shown in FIG. 19. The column fixed type gantry includes a column extending from the floor surface to the ceiling, and the column slides the gantry body. Thought the column fixed type gantry allows imaging of the whole body of a subject in the standing position, it needs a large-sized column extending from the floor surface to the ceiling, which could provide the subject with a feeling of pressure. The column extending to the ceiling decreases the degree of freedom to handle a device attached to the ceiling, such as an injector and makes it difficult to carry the apparatus into a hospital. The column stored type gantry shown in FIG. 19 has a two-stage structure of an upper column and a lower column, and the lower column slides the upper column to raise and lower the gantry body. In the gantry shown in FIG. 19, the upper column can be stored in the lower column, but the gantry body cannot be lowered to the floor surface. Thus, only the upper half of the body of a subject in the standing position can be imaged.

On the other hand, as described above, the gantry 10 according to the present embodiment includes the upper column 27 that supports the gantry body 11 slidably in the longitudinal direction and the lower column 29 that supports the upper column 27 slidably in the longitudinal direction. Unlike the column fixed type gantry shown in FIG. 18, the gantry 10 need not include a column extending from the floor surface to the ceiling, and unlike the gantry body of the column stored type gantry shown in FIG. 19, the gantry body 11 of the gantry 10 can be lowered to the floor surface. In other words, the gantry according to the present embodiment makes it possible to image the whole body of a subject in the standing position without making its size larger than the conventional gantry exclusively for subjects in the lying position.

Therefore, since the gantry 10 and X-ray CT apparatus according to the present embodiment have the structures described above, the whole body of subject S can be imaged without increasing the size of the gantry. Furthermore, since the size of the gantry according to the present embodiment is equal to that of the conventional gantry exclusively for subjects in the lying position, the layout of an examination room need not be changed when the gantry is placed or the walls or ceiling need not be detached when it is carried into the examination room.

In the foregoing descriptions, the column unit 13 has a two-stage structure of the upper and lower columns 27 and 29. However, the present embodiment is not limited to the two-stage structure but may have a multi-stage structure and, in this case, the lower column 29 includes a plurality of lower columns having a nested structure. Each of the lower columns supports inner lower columns slidably in the longitudinal direction. Accordingly, the lower column 29 can be decreased in height.

In conclusion, the X-ray CT apparatus for X-ray CT imaging for subjects in the standing position and the gantry according to the present embodiment make it possible to image the whole body of a subject without increasing the size of the apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
   a gantry configured to image a subject by X-ray CT; and
   a console communicably connected to the gantry,
   wherein the gantry comprises
      a gantry body having a bore into which the subject is inserted when the subject is imaged by X-ray CT;
      a column unit including a first column, which supports the gantry body slidably in a direction perpendicular to a floor surface, and a second column, which supports the first column slidably in a vertical direction,
      a first motor configured to generate power to cause the first column to slide the gantry body;
      a second motor configured to generate power to cause the second column to slide the first column; and
      control circuitry configured to control the first motor and the second motor,
   wherein the first column supports the gantry body slidably within a first movable range;
      the second column supports the first column slidably within a second movable range; and
      the control circuitry is further configured to control the first motor and the second motor synchronously to raise and lower the gantry body within a predetermined range between a maximum height of the gantry body from the floor surface and a minimum height of the gantry body from the floor surface, the maximum height is where the gantry body is located at an upper limit of the first movable range and the first column is located at an upper limit of the second movable range, the minimum height is where the gantry body is located at a lower limit of the first movable range and the first column is located at a lower limit of the second movable range.

2. The X-ray computed tomography apparatus according to claim 1, wherein:
   the first column includes a first slide actuator which supports the gantry body slidably in a longitudinal direction of the first column; and
   the second column includes a second slide actuator which supports the first column slidably in a longitudinal direction of the second column.

3. The X-ray computed tomography apparatus according to claim 1, wherein:
   the first column includes a screw provided along a longitudinal direction of the first column;
   the second column includes a first gear which is engaged with the screw to slide the first column in the vertical direction; and
   a gantry body includes a second gear which is engaged with the screw to slide the gantry body in the vertical direction.

4. The X-ray computed tomography apparatus according to claim 1, wherein the control circuitry is further configured to cause the first column to slide upward in the vertical direction with respect to the second column to extend the column unit, and cause the first column to slide downward in the vertical direction with respect to the second column to contract the column unit.

5. The X-ray computed tomography apparatus according to claim 1, wherein when the predetermined range is wider than one of the first movable range and the second movable range, the control circuitry is further configured to drive the first motor and the second motor in sequence to slide the gantry body.

6. The X-ray computed tomography apparatus according to claim 5, wherein the control circuitry is further configured to gradually switch between the first motor and the second motor within a specific range that is narrower than the predetermined range, the specific range including a middle height of the gantry body from the floor surface when the gantry body is located at the upper limit of the first movable range and the first column is located at the lower limit of the second movable range.

7. The X-ray computed tomography apparatus according to claim 1, wherein when the predetermined range is included in the first movable range, the control circuitry is further configured to drive the first motor to slide the gantry body within the predetermined range.

8. The X-ray computed tomography apparatus according to claim 7, wherein the control circuitry is further configured to drive the second motor to slide the gantry body to a start position in the predetermined range.

9. The X-ray computed tomography apparatus according to claim 1, wherein the control circuitry is further configured to drive the first motor and the second motor simultaneously to slide the gantry body at a velocity which is higher than a velocity of the gantry body when one of the first motor and the second motor is alone driven.

10. The X-ray computed tomography apparatus according to claim 1, wherein:
the first motor is provided at the first column;
the second motor is provided at the second column; and
the control circuitry is provided at one of the first column and the second column.

11. The X-ray computed tomography apparatus according to claim 1, wherein:
the first motor is provided at the first column;
the second motor is provided at the second column; and
the control circuitry is provided at the console.

12. The X-ray computed tomography apparatus according to claim 1, wherein the first column supports the gantry body slidably in a longitudinal direction and supports the gantry body rotatably around a horizontal axis which is horizontally orthogonal to a central axis of the bore.

13. A gantry, comprising:
a gantry body having a bore into which a subject is inserted when the subject is imaged by X-ray CT;
a column unit including a first column, which supports the gantry body slidably in a direction perpendicular to a floor surface, and a second column, which supports the first column slidably in a vertical direction,
a first motor configured to generate power to cause the first column to slide the gantry body;
a second motor configured to generate power to cause the second column to slide the first column; and
control circuitry configured to control the first motor and the second motor,
wherein the first column supports the gantry body slidably within a first movable range;
the second column supports the first column slidably within a second movable range; and
the control circuitry is further configured to control the first motor and the second motor synchronously to raise and lower the gantry body within a predetermined range between a maximum height of the gantry body from the floor surface and a minimum height of the gantry body from the floor surface, the maximum height is where the gantry body is located at an upper limit of the first movable range and the first column is located at an upper limit of the second movable range, the minimum height is where the gantry body is located at a lower limit of the first movable range and the first column is located at a lower limit of the second movable range.

* * * * *